US010363062B2

(12) United States Patent
Spencer et al.

(10) Patent No.: US 10,363,062 B2
(45) Date of Patent: Jul. 30, 2019

(54) ATHERECTOMY CATHETERS AND NON-CONTACT ACTUATION MECHANISM FOR CATHETERS

(71) Applicant: Avinger, Inc., Redwood City, CA (US)

(72) Inventors: Maegan K. Spencer, Menlo Park, CA (US); Nicholas J. Spinelli, San Mateo, CA (US)

(73) Assignee: Avinger, Inc., Redwood City, CA (US)

( * ) Notice: Subject to any disclaimer, the term of this patent is extended or adjusted under 35 U.S.C. 154(b) by 244 days.

(21) Appl. No.: 13/654,357

(22) Filed: Oct. 17, 2012

(65) Prior Publication Data

US 2013/0096589 A1    Apr. 18, 2013

Related U.S. Application Data

(60) Provisional application No. 61/548,179, filed on Oct. 17, 2011, provisional application No. 61/646,843, filed on May 14, 2012.

(51) Int. Cl.
*A61B 17/3207* (2006.01)
*A61B 17/22* (2006.01)
*A61B 17/00* (2006.01)
*A61B 17/29* (2006.01)
*A61B 90/00* (2016.01)

(52) U.S. Cl.
CPC ........... *A61B 17/320758* (2013.01); *A61B 2017/00057* (2013.01); *A61B 2017/00398* (2013.01); *A61B 2017/00876* (2013.01); *A61B 2017/22039* (2013.01); *A61B 2017/22094* (2013.01); *A61B 2017/2927* (2013.01); *A61B 2017/320791* (2013.01); *A61B 2090/0813* (2016.02);

(Continued)

(58) Field of Classification Search
CPC .. A61B 17/320758; A61B 2017/22039; A61B 2017/320791; A61B 2017/22094; A61B 2019/5234; A61M 2025/0161
See application file for complete search history.

(56) References Cited

U.S. PATENT DOCUMENTS

| 3,908,637 A | 9/1975 | Doroshow |
| 4,178,935 A | 12/1979 | Gekhaman et al. |

(Continued)

FOREIGN PATENT DOCUMENTS

| CN | 1875242 A | 12/2006 |
| CN | 1947652 A | 4/2007 |

(Continued)

OTHER PUBLICATIONS

Simpson et al.; U.S. Appl. No. 14/171,583 entitled "Occlusion-Crossing Devices, Imaging, and Atherectomy Devices," filed Feb. 3, 2014.

(Continued)

*Primary Examiner* — Alexander J Orkin
(74) *Attorney, Agent, or Firm* — Shay Glenn LLP

(57) ABSTRACT

An atherectomy catheter includes a deflectable distal tip, a rotatable cutter proximal to the distal tip, a cutter drive shaft configured to rotate the rotatable cutter, and a pull shaft concentric with the drive shaft and coupled to the distal tip. The pull shaft is configured such that pulling the pull shaft deflects the distal tip, thereby exposing the rotatable cutter. Also disclosed herein is a magnetic drive system configured for non-contact actuation of a catheter.

14 Claims, 36 Drawing Sheets

(52) U.S. Cl.
CPC .............. *A61B 2090/3614* (2016.02); *A61B 2090/3735* (2016.02)

(56) References Cited

U.S. PATENT DOCUMENTS

| | | | |
|---|---|---|---|
| 4,487,206 A | 12/1984 | Aagard | |
| 4,527,553 A | 7/1985 | Upsher | |
| 4,552,554 A | 11/1985 | Gould et al. | |
| 4,621,353 A | 11/1986 | Hazel et al. | |
| 4,639,091 A | 1/1987 | Huignard et al. | |
| 4,654,024 A | 3/1987 | Crittenden et al. | |
| 4,686,982 A | 8/1987 | Nash | |
| 4,691,708 A | 9/1987 | Kane | |
| 4,771,774 A | 9/1988 | Simpson et al. | |
| 4,841,977 A | 6/1989 | Griffith et al. | |
| 4,857,046 A | 8/1989 | Stevens et al. | |
| 4,920,961 A | 5/1990 | Grossi et al. | |
| 4,926,858 A | 5/1990 | Gifford, III et al. | |
| 5,000,185 A | 3/1991 | Yock | |
| 5,018,529 A | 5/1991 | Tenerz et al. | |
| 5,041,082 A | 8/1991 | Shiber | |
| 5,047,040 A | 9/1991 | Simpson et al. | |
| 5,085,662 A | 2/1992 | Willard | |
| 5,099,850 A | 3/1992 | Matsui et al. | |
| 5,178,153 A | 1/1993 | Einzig | |
| 5,182,291 A | 1/1993 | Gubin et al. | |
| 5,190,050 A | 3/1993 | Nitzsche | |
| 5,192,291 A | 3/1993 | Pannek, Jr. | |
| 5,312,415 A | 5/1994 | Palermo | |
| 5,312,425 A | 5/1994 | Evans et al. | |
| 5,321,501 A | 6/1994 | Swanson et al. | |
| 5,333,142 A | 7/1994 | Scheps | |
| 5,358,472 A | 10/1994 | Vance et al. | |
| 5,366,464 A | 11/1994 | Belknap | |
| 5,383,460 A | 1/1995 | Jang et al. | |
| 5,383,467 A | 1/1995 | Auer et al. | |
| 5,425,273 A | 6/1995 | Chevalier | |
| 5,429,136 A | 7/1995 | Milo et al. | |
| 5,431,673 A * | 7/1995 | Summers et al. | 606/170 |
| 5,437,284 A | 8/1995 | Trimble | |
| 5,459,570 A | 10/1995 | Swanson et al. | |
| 5,460,168 A * | 10/1995 | Masubuchi | A61B 1/00096 600/107 |
| 5,465,147 A | 11/1995 | Swanson | |
| 5,507,795 A | 4/1996 | Chiang et al. | |
| 5,556,405 A | 9/1996 | Lary | |
| 5,607,394 A | 3/1997 | Andersen et al. | |
| 5,620,426 A | 4/1997 | Braithwaite | |
| 5,632,754 A | 5/1997 | Farley et al. | |
| 5,632,755 A | 5/1997 | Nordgren et al. | |
| 5,674,232 A | 10/1997 | Halliburton | |
| 5,681,336 A | 10/1997 | Clement et al. | |
| 5,690,634 A | 11/1997 | Muller et al. | |
| 5,722,403 A | 3/1998 | McGee et al. | |
| 5,795,295 A | 8/1998 | Hellmuth et al. | |
| 5,807,339 A | 9/1998 | Bostrom et al. | |
| 5,830,145 A | 11/1998 | Tenhoff | |
| 5,836,957 A | 11/1998 | Schulz et al. | |
| 5,843,050 A | 12/1998 | Jones et al. | |
| 5,843,103 A | 12/1998 | Wulfman | |
| 5,868,778 A | 2/1999 | Gershony et al. | |
| 5,872,879 A | 2/1999 | Hamm | |
| 5,904,651 A | 5/1999 | Swanson et al. | |
| 5,907,425 A | 5/1999 | Dickensheets et al. | |
| 5,935,075 A | 8/1999 | Casscells et al. | |
| 5,938,602 A | 8/1999 | Lloyd | |
| 5,951,482 A | 9/1999 | Winston et al. | |
| 5,951,581 A | 9/1999 | Saadat et al. | |
| 5,951,583 A | 9/1999 | Jensen et al. | |
| 5,956,355 A | 9/1999 | Swanson et al. | |
| 5,957,952 A | 9/1999 | Gershony et al. | |
| 5,987,995 A | 11/1999 | Sawatari et al. | |
| 5,997,558 A | 12/1999 | Nash | |
| 6,001,112 A | 12/1999 | Taylor | |
| 6,007,530 A | 12/1999 | Dornhofer et al. | |
| 6,010,449 A | 1/2000 | Selmon et al. | |
| 6,013,072 A | 1/2000 | Winston et al. | |
| 6,017,359 A | 1/2000 | Gershony et al. | |
| 6,027,514 A | 2/2000 | Stine et al. | |
| 6,032,673 A | 3/2000 | Savage et al. | |
| 6,048,349 A | 4/2000 | Winston et al. | |
| 6,080,170 A | 6/2000 | Nash et al. | |
| 6,106,515 A | 8/2000 | Winston et al. | |
| 6,110,164 A | 8/2000 | Vidlund | |
| 6,120,515 A | 9/2000 | Rogers et al. | |
| 6,120,516 A | 9/2000 | Selmon et al. | |
| 6,134,002 A | 10/2000 | Stimson et al. | |
| 6,134,003 A | 10/2000 | Tearney et al. | |
| 6,152,938 A | 11/2000 | Curry | |
| 6,152,951 A | 11/2000 | Hashimoto et al. | |
| 6,160,826 A | 12/2000 | Swanson et al. | |
| 6,175,669 B1 | 1/2001 | Colston et al. | |
| 6,176,871 B1 | 1/2001 | Pathak et al. | |
| 6,183,432 B1 | 2/2001 | Milo | |
| 6,193,676 B1 | 2/2001 | Winston et al. | |
| 6,206,898 B1 | 3/2001 | Honeycutt et al. | |
| 6,228,076 B1 | 5/2001 | Winston et al. | |
| 6,241,744 B1 | 6/2001 | Imran et al. | |
| 6,283,957 B1 | 9/2001 | Hashimoto et al. | |
| 6,290,668 B1 | 9/2001 | Gregory et al. | |
| 6,294,775 B1 | 9/2001 | Seibel et al. | |
| 6,299,622 B1 | 10/2001 | Snow et al. | |
| 6,307,985 B1 | 10/2001 | Murakami et al. | |
| 6,402,719 B1 | 6/2002 | Ponzi et al. | |
| 6,416,527 B1 | 7/2002 | Berg et al. | |
| 6,445,939 B1 | 9/2002 | Swanson et al. | |
| 6,445,944 B1 | 9/2002 | Ostrovsky | |
| 6,447,525 B2 | 9/2002 | Follmer et al. | |
| 6,451,036 B1 | 9/2002 | Heitzmann et al. | |
| 6,454,717 B1 | 9/2002 | Pantages et al. | |
| 6,454,779 B1 | 9/2002 | Taylor | |
| 6,482,216 B1 | 11/2002 | Hiblar et al. | |
| 6,482,217 B1 | 11/2002 | Pintor et al. | |
| 6,485,413 B1 | 11/2002 | Boppart et al. | |
| 6,497,649 B2 | 12/2002 | Parker et al. | |
| 6,501,551 B1 | 12/2002 | Tearney et al. | |
| 6,503,261 B1 | 1/2003 | Bruneau et al. | |
| 6,511,458 B2 | 1/2003 | Milo et al. | |
| 6,517,528 B1 | 2/2003 | Pantages et al. | |
| 6,542,665 B2 | 4/2003 | Reed et al. | |
| 6,546,272 B1 | 4/2003 | MacKinnon et al. | |
| 6,551,302 B1 | 4/2003 | Rosinko et al. | |
| 6,563,105 B2 | 5/2003 | Seibel et al. | |
| 6,564,087 B1 | 5/2003 | Pitris et al. | |
| 6,565,588 B1 | 5/2003 | Clement et al. | |
| 6,572,563 B2 | 6/2003 | Ouchi et al. | |
| 6,572,643 B1 | 6/2003 | Gharibadeh | |
| 6,575,995 B1 | 6/2003 | Huter et al. | |
| 6,579,298 B1 | 6/2003 | Bruneau et al. | |
| 6,615,071 B1 | 9/2003 | Casscells, III et al. | |
| 6,638,233 B2 | 10/2003 | Corvi et al. | |
| 6,645,217 B1 | 11/2003 | MacKinnon et al. | |
| 6,657,727 B1 | 12/2003 | Izatt et al. | |
| 6,666,874 B2 | 12/2003 | Heitzmann et al. | |
| 6,687,010 B1 | 2/2004 | Horii | |
| 6,728,571 B1 | 4/2004 | Barbato | |
| D489,973 S | 5/2004 | Root et al. | |
| 6,730,063 B2 | 5/2004 | Delaney et al. | |
| 6,758,854 B1 | 7/2004 | Butler et al. | |
| 6,760,112 B2 | 7/2004 | Reed et al. | |
| 6,800,085 B2 | 10/2004 | Selmon et al. | |
| 6,818,001 B2 | 11/2004 | Wulfman et al. | |
| 6,824,550 B1 | 11/2004 | Noriega et al. | |
| 6,830,577 B2 | 12/2004 | Nash et al. | |
| 6,845,190 B1 | 1/2005 | Smithwick et al. | |
| 6,852,109 B2 | 2/2005 | Winston et al. | |
| 6,853,457 B2 | 2/2005 | Bjarklev et al. | |
| 6,856,712 B2 | 2/2005 | Fauver et al. | |
| 6,867,753 B2 | 3/2005 | Chinthammit et al. | |
| 6,879,851 B2 | 4/2005 | McNamara et al. | |
| 6,947,787 B2 | 9/2005 | Webler | |
| 6,961,123 B1 | 11/2005 | Wang et al. | |
| 6,970,732 B2 | 11/2005 | Winston et al. | |
| 6,975,898 B2 | 12/2005 | Seibel | |

(56) References Cited

U.S. PATENT DOCUMENTS

| | | |
|---|---|---|
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2* | 3/2010 | Martin .................. A61B 50/30 600/139 |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,027,714 B2 | 9/2011 | Shachar |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,603 B2 | 10/2013 | Swoyer et al. |
| 8,632,557 B2 | 1/2014 | Thatcher et al. |
| 8,911,459 B2 | 12/2014 | Simpson et al. |
| 9,119,662 B2 | 9/2015 | Moberg |
| 9,351,757 B2 | 5/2016 | Kusleika |
| 2001/0020126 A1 | 9/2001 | Swanson et al. |
| 2002/0019644 A1* | 2/2002 | Hastings et al. .............. 606/159 |
| 2002/0072706 A1 | 6/2002 | Hiblar et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1* | 8/2005 | Simpson ....................... 600/564 |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |

(56) References Cited

U.S. PATENT DOCUMENTS

| | | |
|---|---|---|
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045892 A1 | 2/2008 | Ferry et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0125019 A1* | 5/2009 | Douglass .......... A61B 18/1482 606/41 |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1* | 11/2009 | Bielewicz .......... A61B 8/12 600/424 |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0080016 A1 | 4/2010 | Fukui et al. |
| 2010/0125253 A1 | 5/2010 | Olson et al. |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0274270 A1 | 10/2010 | Patel et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0023617 A1 | 2/2011 | Miao et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0257478 A1 | 10/2011 | Kleiner et al. |
| 2011/0263936 A1 | 10/2011 | He et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0253186 A1 | 10/2012 | Simpson et al. |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0123615 A1 | 5/2013 | Spencer et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0296695 A1 | 11/2013 | Spencer et al. |
| 2013/0317519 A1 | 11/2013 | Romo et al. |
| 2014/0371718 A1 | 12/2014 | Alvarez et al. |
| 2015/0025310 A1 | 1/2015 | Everingham et al. |
| 2015/0208922 A1 | 7/2015 | Newhauser et al. |
| 2016/0008025 A1 | 1/2016 | Gupta et al. |
| 2016/0029902 A1 | 2/2016 | Smith et al. |
| 2016/0038030 A1 | 2/2016 | Smith et al. |
| 2017/0065293 A1 | 3/2017 | Rosenthal et al. |
| 2017/0065295 A1 | 3/2017 | Patel et al. |
| 2017/0238803 A1 | 8/2017 | Kankaria |
| 2017/0238808 A1 | 8/2017 | Simpson et al. |
| 2017/0273711 A1 | 9/2017 | Simpson et al. |
| 2018/0192880 A1 | 7/2018 | Patel et al. |
| 2018/0207417 A1 | 7/2018 | Zung et al. |
| 2018/0256039 A1 | 9/2018 | Smith et al. |
| 2018/0256187 A1 | 9/2018 | Patel et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | S62-275425 A | 11/1987 |
| JP | 03502060 A | 2/1990 |
| JP | 05103763 A | 4/1993 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |

(56) References Cited

FOREIGN PATENT DOCUMENTS

| | | |
|---|---|---|
| JP | 2005-249704 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-83057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2010042182 A | 2/2010 |
| JP | 2010518900 A | 6/2010 |
| JP | 2011521747 A | 7/2011 |
| JP | 2012533353 A | 12/2012 |
| KR | 2007/0047221 | 5/2007 |
| RU | 2185859 C2 | 7/2002 |
| RU | 2218191 C2 | 12/2003 |
| WO | WO 91/017698 A1 | 11/1991 |
| WO | WO 99/23958 A1 | 5/1999 |
| WO | WO 00/54659 A1 | 9/2000 |
| WO | WO01/15609 A1 | 3/2001 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A | 3/2008 |
| WO | WO 2008/042987 A2 | 4/2008 |
| WO | WO2008/051951 A1 | 5/2008 |
| WO | WO 2008/065600 A2 | 6/2008 |
| WO | WO 2008/086613 A1 | 7/2008 |
| WO | WO 2008/087613 A2 | 7/2008 |
| WO | WO2009/005779 A1 | 1/2009 |
| WO | WO 2009/006335 A1 | 1/2009 |
| WO | WO 2009/009799 A1 | 1/2009 |
| WO | WO 2009/009802 A1 | 1/2009 |
| WO | WO 2009/023635 A | 2/2009 |
| WO | WO 2009/024344 A1 | 2/2009 |
| WO | WO 2009/094341 A2 | 7/2009 |
| WO | WO 2009/140617 A2 | 11/2009 |
| WO | WO2009/148317 A1 | 12/2009 |
| WO | WO 2010/039464 A1 | 4/2010 |
| WO | WO 2010/056771 A1 | 5/2010 |
| WO | WO 2011/044387 A2 | 4/2011 |
| WO | WO 2012/061935 A1 | 5/2012 |
| WO | WO2012/166332 A1 | 12/2012 |
| WO | WO2013/033490 A1 | 3/2013 |

OTHER PUBLICATIONS

Gonzalo et al.; Optical coherence tomography patterns of stent restenosis; Am. Heart J.; 158(2); pp. 284-293; Aug. 2009.
Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.
Kankaria; U.S. Appl. No. 14/400,140 entitled "Optical coherence tomography with index fiber for biological imaging," filed Nov. 10, 2014.
Gupta et al.; U.S. Appl. No. 14/401,175 entitled "Atherectomy catheters with imaging," filed Nov. 14, 2014.
Tachibana et al.; U.S. Appl. No. 14/400,151 entitled "Atherectomy catheter drive assemblies," filed Nov. 10, 2014.
Patel et al.; U.S. Appl. No. 13/929,579 entitled "Guidewire Positioning Catheter," filed Jun. 27, 2013.
He et al.; U.S. Appl. No. 14/019,466 entitled "Devices and Methods for Predicting and Preventing Restenosis," filed Sep. 5, 2013.
Patel et al.; U.S. Appl. No. 13/752,325 entitled "Catheter system and method for boring through blocked vascular passages," filed Jan. 28, 2013.
Aziz et al.; Chronic total occlusions—a stiff challenge requiring a major breakthrough: is there light at the end of the tunnel?; Heart; vol. 91; suppl. III; pp. 42-48; Jun. 2005.
Emkey et al.; Analysis and evaluation of graded-index fiber-lenses; Journal of Lightwave Technology; vol. LT-5; No. 9; pp. 1156-1164; Sep. 1987.
Linares et al.; Arbitrary single-mode coupling by tapered and nontapered grin fiber lenses; Applied Optics; vol. 29; No. 28; pp. 4003-4007; Oct. 1, 1990.
Sharma et al.; Optical coherence tomography based on an all-fiber autocorrelator using probe-end reflection as reference; CWJ13; San Francisco, California; CLEO May 16, 2004; 4 pages.
Suparno et al.; Light scattering with single-mode fiber collimators; Applied Optics; vol. 33; No. 30; pp. 7200-7205; Oct. 20, 1994.
Han et al.; In situ Frog Retina Imaging Using Common-Path OCT with a Gold-Coated Bare Fiber Probe; CFM6; San Jose, California; CLEO, May 4, 2008; 2 pages.
Muller et al.; Time-gated infrared fourier-domain optical coherence tomography; CFM5; San Jose, California; CLEO May 4, 2008; 2 pages.
Wang et al.; Common-path endoscopic Fourier domain OCT with a reference Michelson interferometer; Proceedings of the SPIE; vol. 7566; pp. 75660L-75660L-7; Jan. 2010.
Simpson et al.; U.S. Appl. No. 14/424,266 entitled "Re-entry stylet for catheter," filed Feb. 26, 2015.
Simpson et al.; U.S. Appl. No. 14/424,277 entitled "Balloon atherectomy catheters with imaging," filed Feb. 26, 2015.
Patel et al.; U.S. Appl. No. 15/162,330 entitled "Atherectomy catheters with longitudinally displaceable drive shafts," filed May 23, 2016.
Spencer et al.; U.S. Appl. No. 15/162,353 entitled "Occlusion-crossing devices, atherectomy devices, and imaging," filed May 23, 2016.
Tachibana et al.; U.S. Appl. No. 15/162,391 entitled "Atherectomy catheter drive assemblies," filed May 23, 2016.
Simpson et al.; U.S. Appl. No. 15/072,272 entitled "Atherectomy catheters devices having multi-channel bushings," filed Mar. 16, 2016.
Patel et al.; U.S. Appl. No. 15/076,568 entitled "Atherectomy catheters and occlusion crossing devices," filed Mar. 21, 2016.
Simpson et al.; U.S. Appl. No. 14/899,877 entitled "Occlusion sheath for imaging catheter," filed Dec. 18, 2015.
Simpson et al.; U.S. Appl. No. 14/899,893 entitled "Identification of elastic lamina to guide interventional therapy," filed Dec. 18, 2015.
Shinkle et al.; Evaluation of stent placement and outcomes with optical coherence tomography; Interv. Cardiol.; 2(4); pp. 535-543; (manuscript version, 12 pages); Aug. 2010.
Patel et al.; U.S. Appl. No. 15/324,325 entitled "High speed chronic total occulusion crossing devices," filed Jan. 6, 2017.
Patel et al.; U.S. Appl. No. 15/480,238 entitled "Guidewire positioning catheter," filed Apr. 5, 2017.
Black et al.; U.S. Appl. No. 15/783,800 entitled "Optical coherence tomography for biological imaging," filed Oct. 13, 2017.
Newhauser et al.; U.S. Appl. No. 15/954,407 entitled "Occlusion-crossing devices," filed Apr. 16, 2018.
Christensen; U.S. Appl. No. 16/069,545 entitled "OCT imaging catheter with lag correction," filed Jul. 12, 2018.
Rosenthal et al.; U.S. Appl. No. 16/105,743 entitled "Atherectomy catheter with laterally-displaceable tip," filed Aug. 20, 2018.
Patel et al.; U.S. Appl. No. 16/148,246 entitled "Atherectomy catheter with serrated cutter," filed Oct. 1, 2018.

* cited by examiner

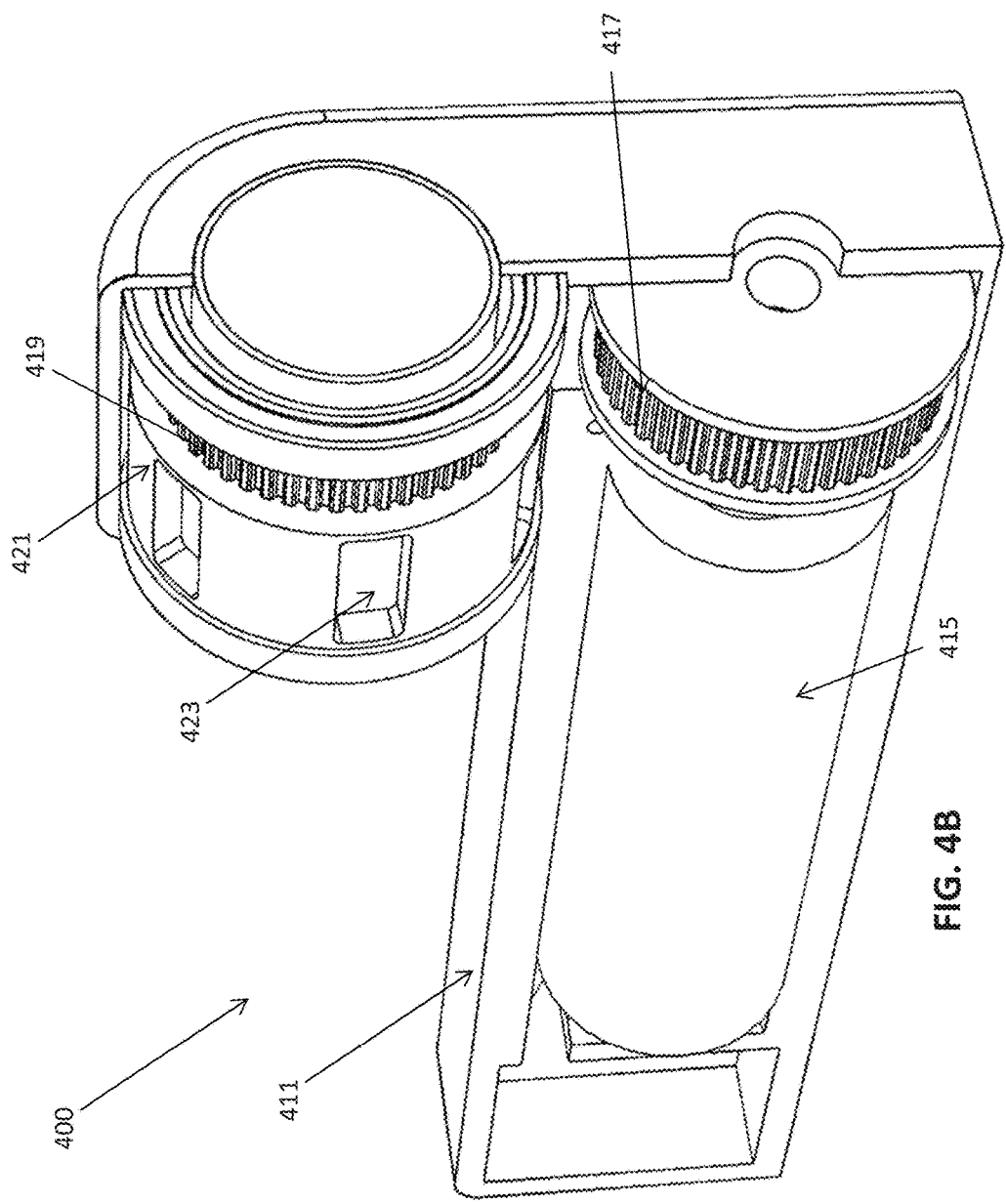

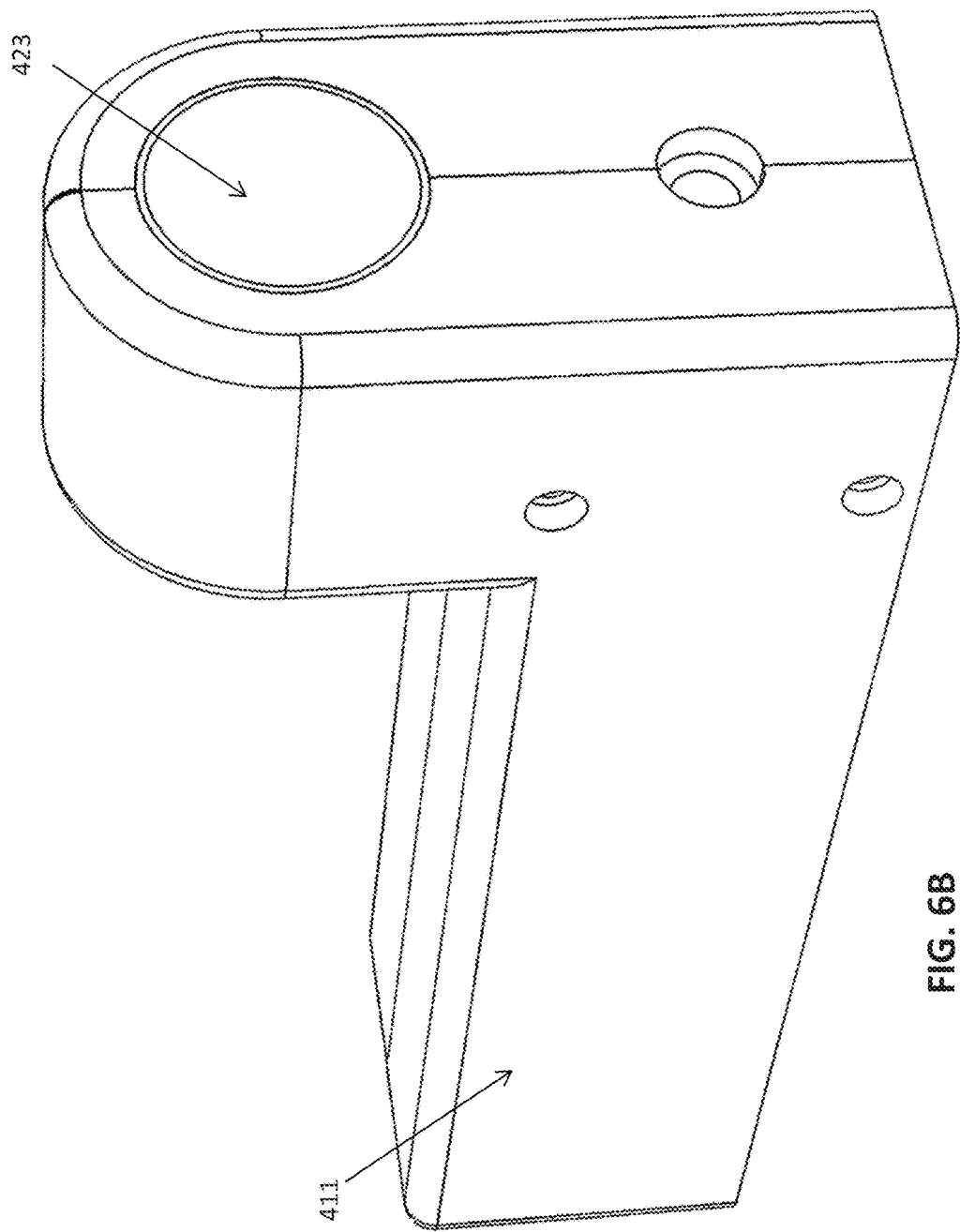

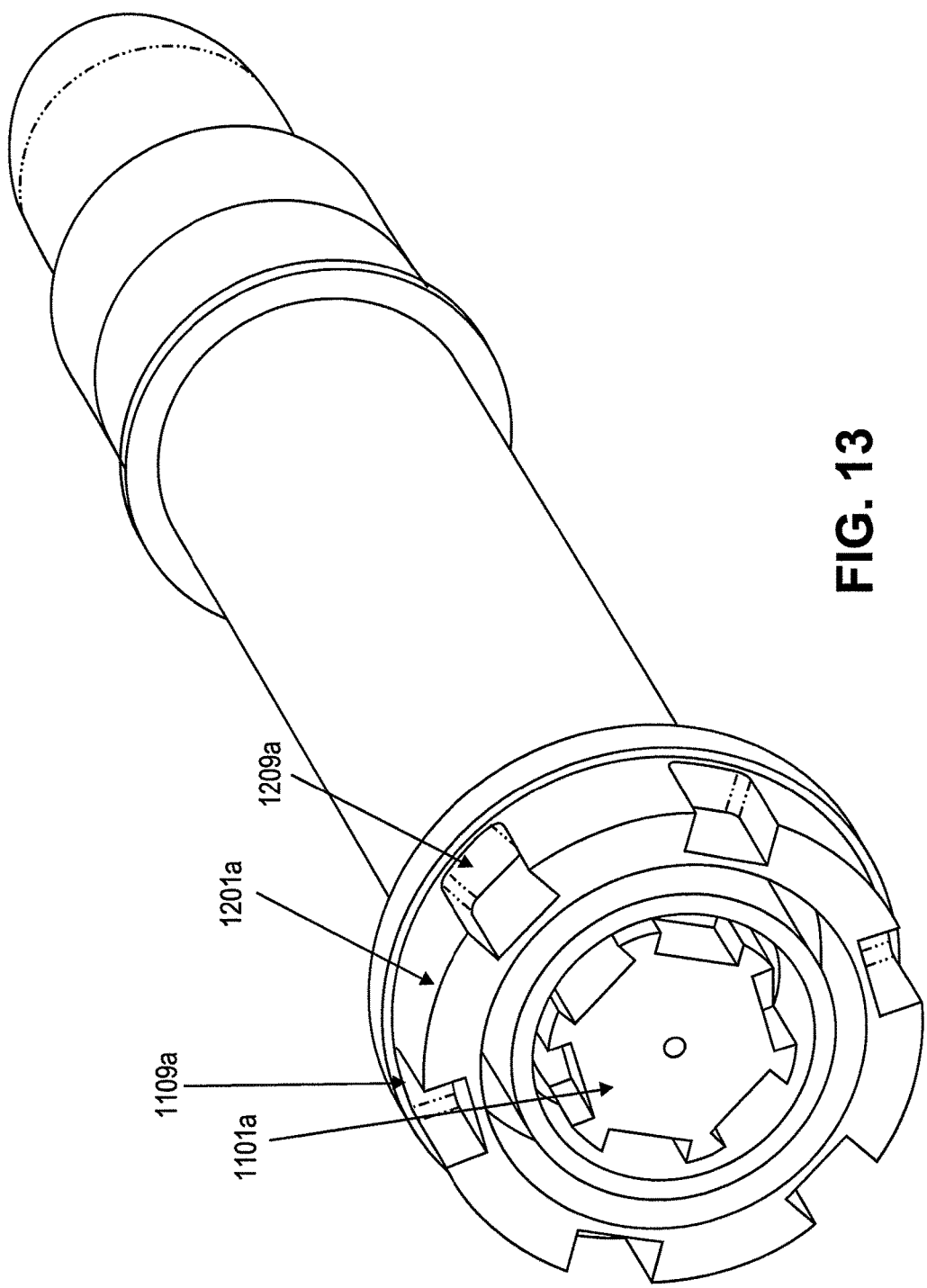

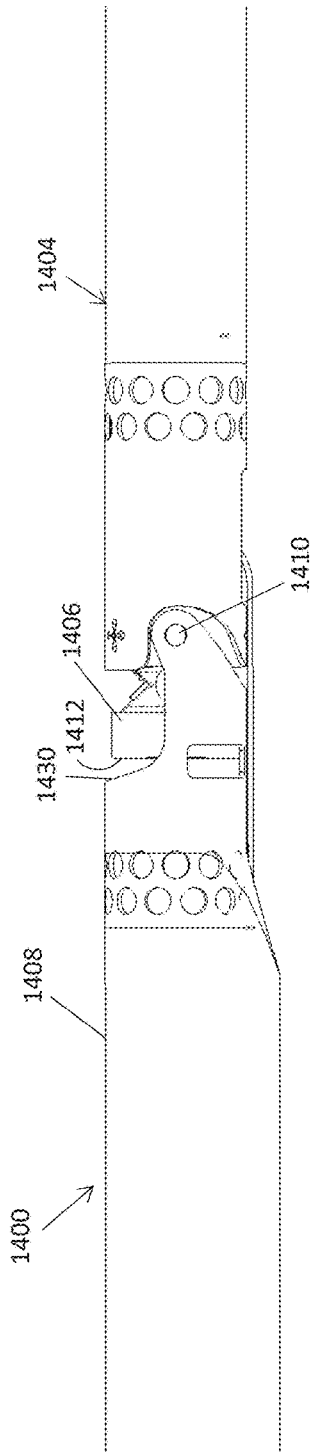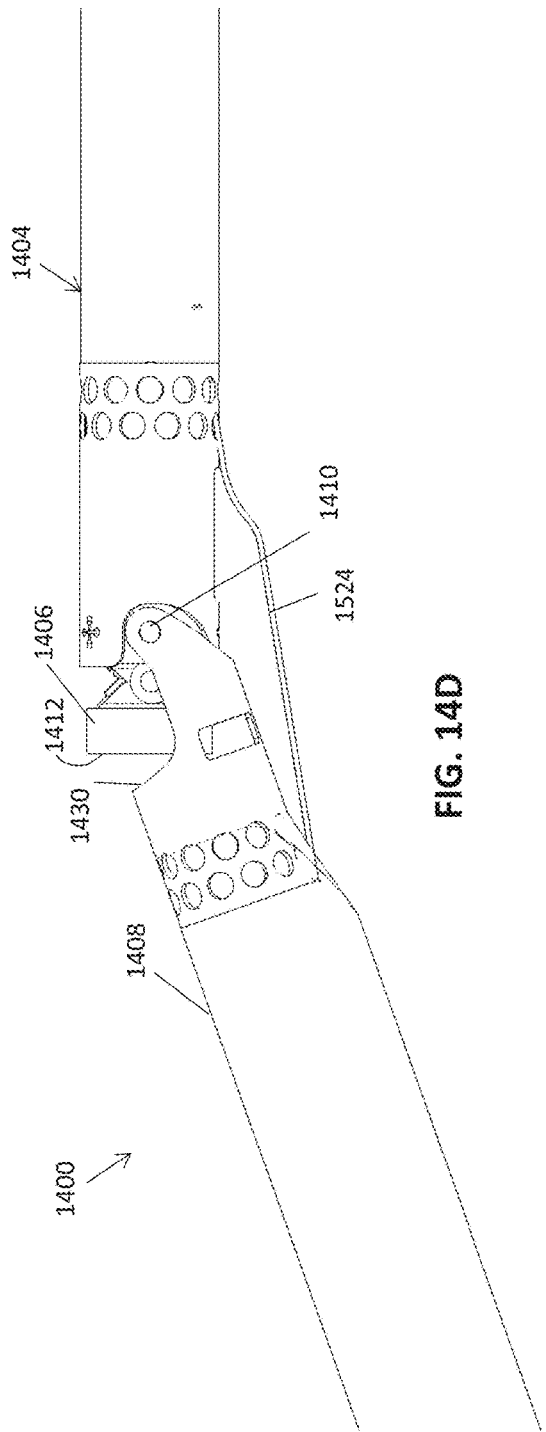

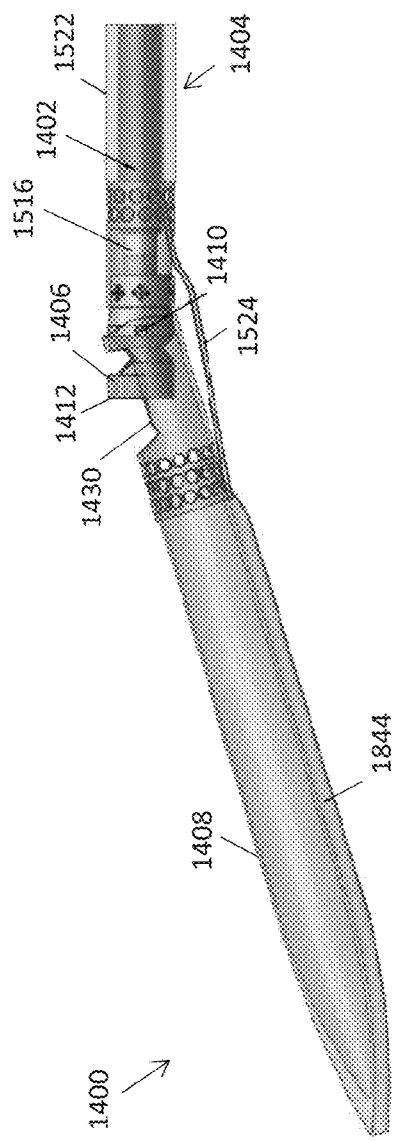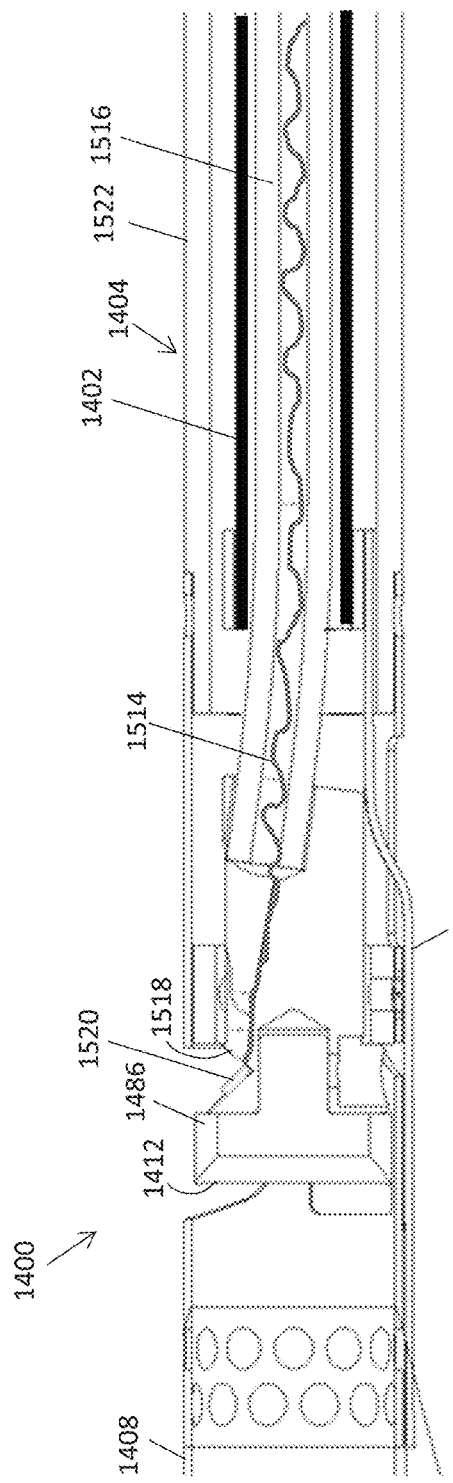

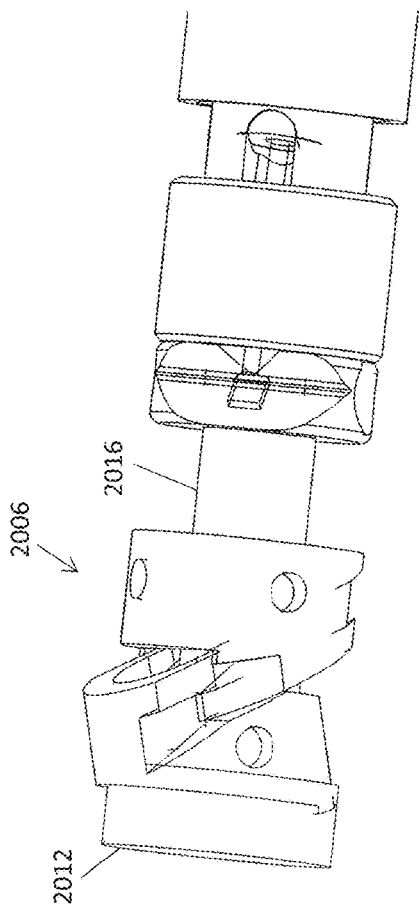
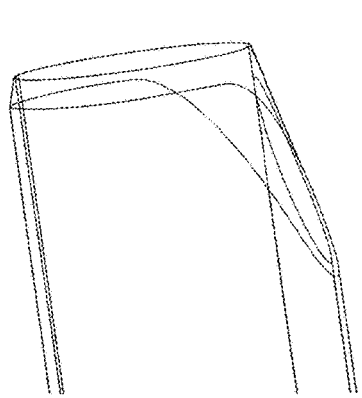
FIG. 20E
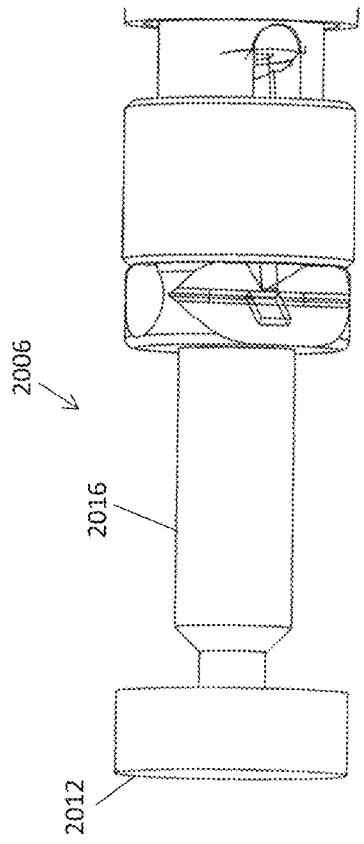
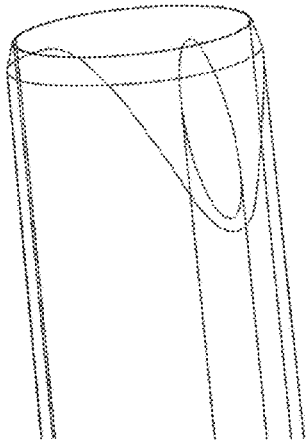
FIG. 20F

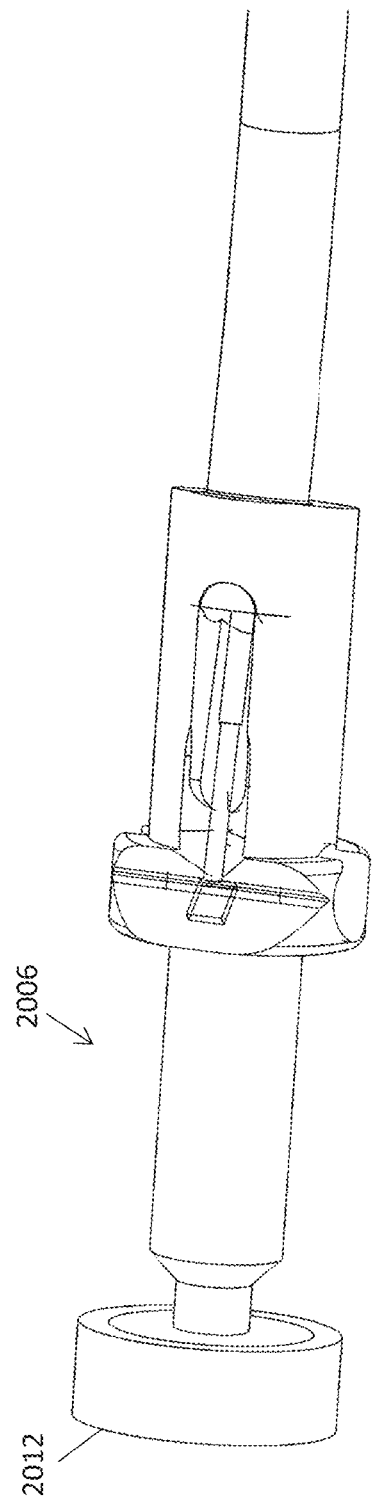

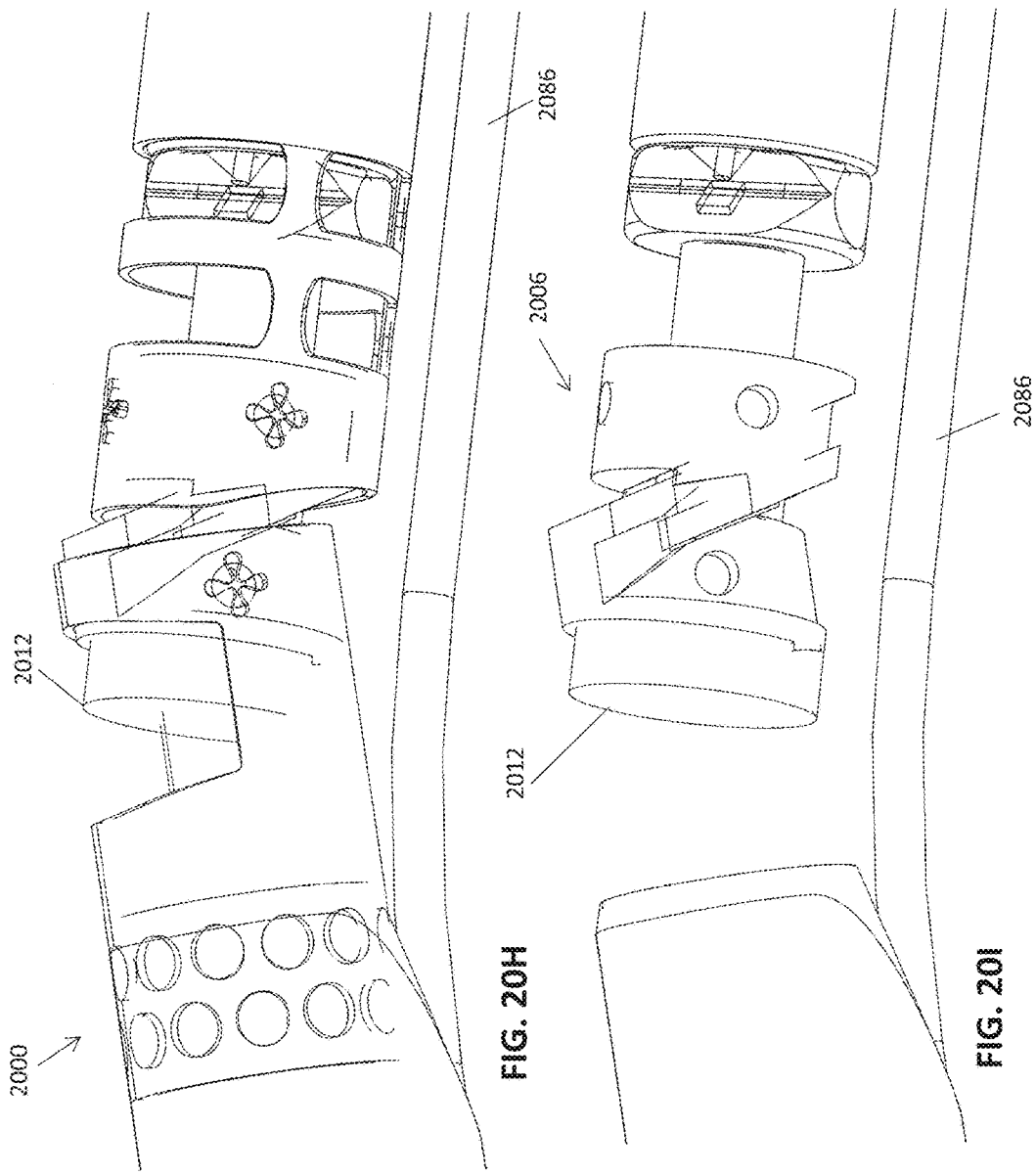

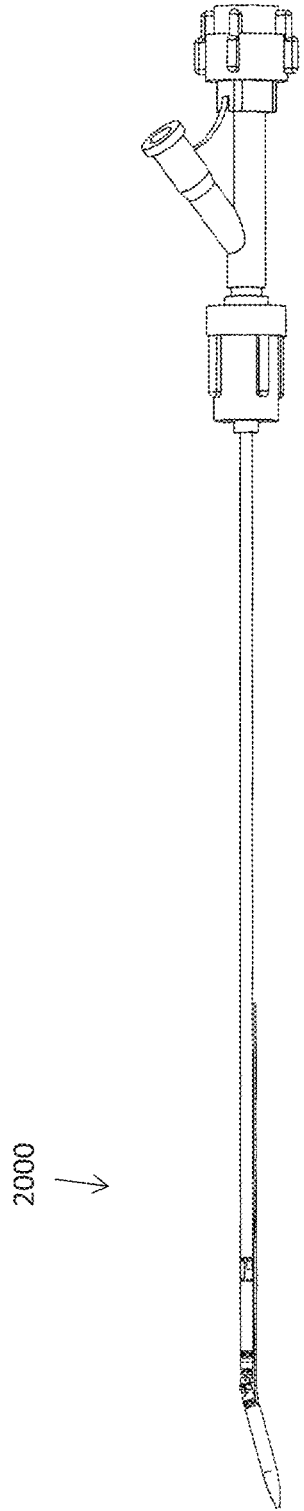
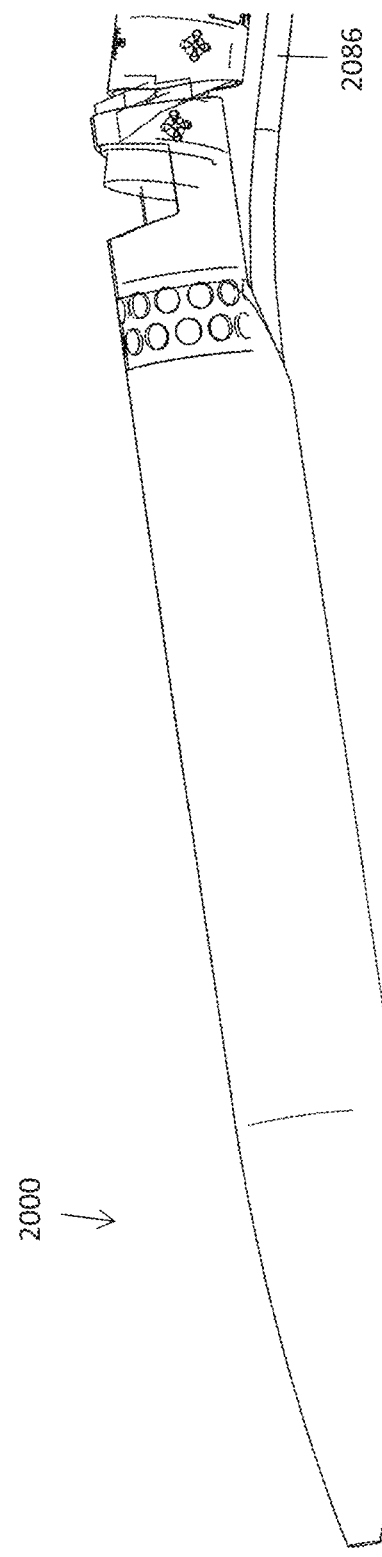

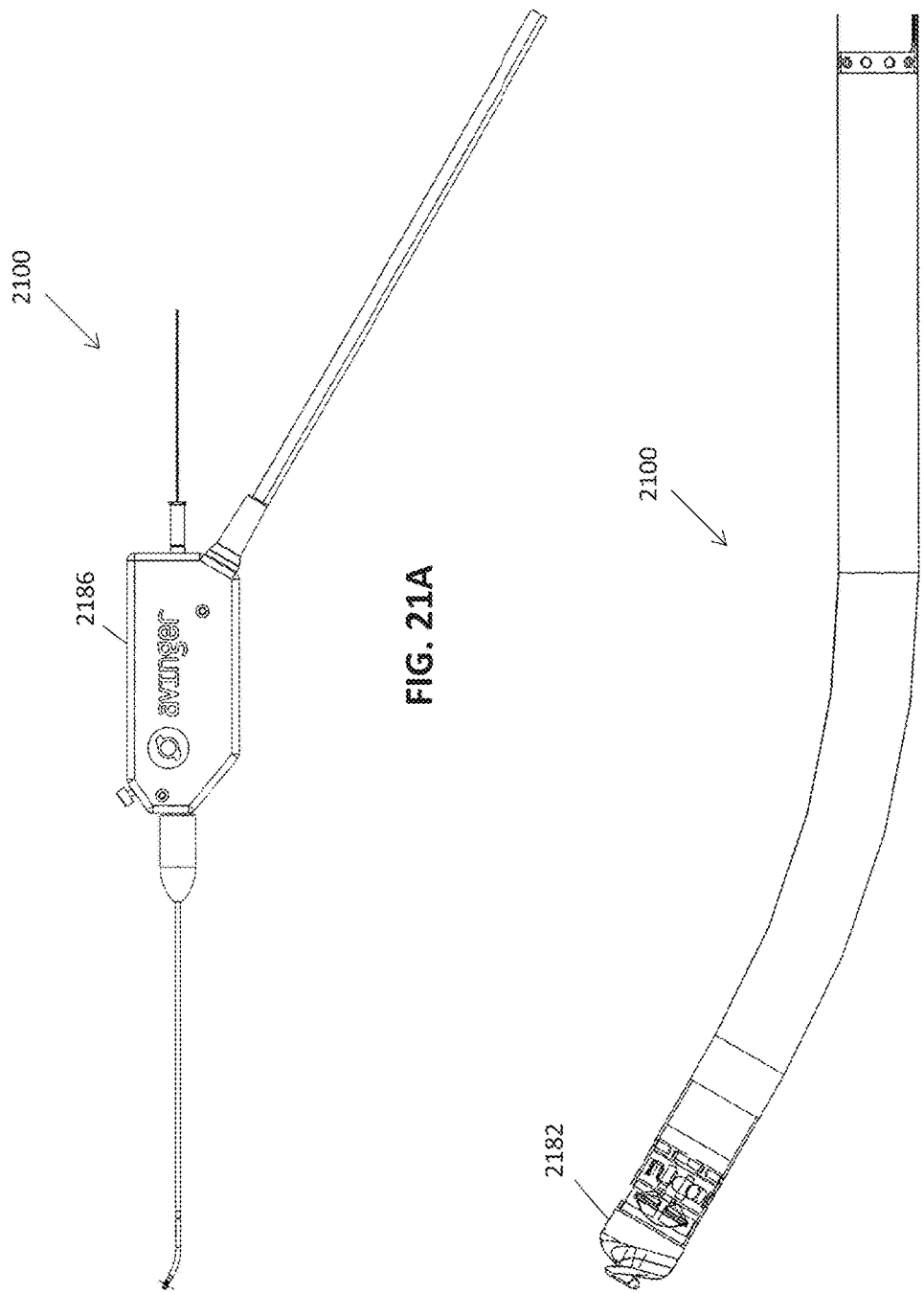

ATHERECTOMY CATHETERS AND NON-CONTACT ACTUATION MECHANISM FOR CATHETERS

CROSS REFERENCE TO RELATED APPLICATIONS

This patent application claims priority to U.S. provisional patent application No. 61/548,179, filed Oct. 17, 2011 and titled "OCCLUSION-CROSSING DEVICES, IMAGING, AND ATHERECTOMY DEVICES," which is incorporated by reference in its entirety. This application also claims priority to U.S. provisional patent application No. 61/646,843, filed May 14, 2012 and titled "ATHERECTOMY CATHETERS WITH IMAGING," which is incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are atherectomy catheters. More specifically, described herein are atherectomy catheters including a pull shaft and pull-wire mechanism configured to deflect a distal end region of the catheter and expose a cutter. Also described herein are non-contact mechanisms for driving catheters, such as occlusion-crossing and atherectomy catheters. More specifically, described herein are non-contact magnetic drive systems for controlling motion (e.g., rotation of the cutting and/or imaging elements) of the catheter without contacting catheter, thereby maintaining sterility of the catheter even when using a non-sterile driver.

BACKGROUND

Peripheral artery disease (PAD) affects millions of people in the United States alone. PAD is a silent, dangerous disease that can have catastrophic consequences when left untreated. PAD is the leading cause of amputation in patients over 50 and is responsible for approximately 160,000 amputations in the United States each year.

Peripheral artery disease (PAD) is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. The most significant of these occlusions are called chronic total occlusions (CTO). Blood circulation to the brain and heart may be reduced by CTOs, increasing the risk for stroke and heart disease.

Interventional treatments for PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and is positioned such that the balloon resides within the blockage. The balloon, connected to the catheter, is expanded to open the artery. Surgeons may then place a wire mesh tube, called a stent, at the area of blockage to keep the artery open.

Traditional atherectomy devices have been plagued by a number of problems that have severely limited market adoption of these devices. These challenges include the following: (1) the need for large vessel access devices; (2) the presence of rigid distal assembles, which make device introduction and control challenging; (3) the need for a fixed and predictable cut length; (4) the need for predictable cut depth; (5) the desire for sufficient tissue collection and removal; and (6) the need for simplified user operation. The systems and devices described herein may overcome these hurdles and give physicians a safe, reliable, and simple cutting system that enables the precision required in eccentric lesions, various disease states, and tortuous anatomy.

Further, many minimally invasive techniques (e.g., atherectomy, angioplasty, etc.) require either rotational and/or longitudinal motion of components (e.g. for cutting, imaging, and/or packing of tissue). Such activation, however, generally requires use of a drive system connected to the catheter. Disposable drive systems, however, are expensive and impractical. On the other hand, reusable drive systems can be problematic for keeping the surgical field sterile. What is needed, therefore, is a reusable drive system that can easily be kept in the sterile field.

SUMMARY OF THE DISCLOSURE

The present invention also relates to atherectomy catheters configured to cut occlusive material from a vessel using a rotational cutter. The rotational cutter can be exposed through deflection of the distal tip by a pull shaft connected to a nosecone, such as through a pull-wire. The rotational cutter may have a circular (e.g., ring-shaped) profile.

In general, in one aspect, an atherectomy catheter includes a deflectable distal tip, a rotatable cutter proximal to the distal tip, a cutter drive shaft configured to rotate the rotatable cutter, and a pull shaft concentric with the drive shaft and coupled to the distal tip. The pull shaft is configured such that pulling the pull shaft deflects the distal tip, thereby exposing the rotatable cutter.

This and other embodiments can include one or more of the following features. The atherectomy catheter can include an optical fiber for optical coherence tomography (OCT) imaging coupled to the rotatable cutter. The drive shaft can be hollow, and an optical fiber for OCT imaging can extend within the drive shaft. The optical fiber can be attached to the rotatable cutter but be otherwise free to float within the drive shaft. The optical fiber can extend off-axis from the drive shaft. The pull shaft can be coupled to the distal tip through a pull-wire connected to both the distal tip and the pull shaft. The pull shaft and pull-wire can be movable with respect to the drive shaft. The atherectomy catheter can further include an outer shaft coupled to the distal tip through a hinge mechanism. The pull shaft can be concentric with the outer shaft and be located between the drive shaft and the outer shaft. The pull shaft can be configured to deflect the distal tip without impacting the directionality of the catheter.

In general, in one aspect, an atherectomy catheter includes a catheter body, a deflectable distal tip, a rotatable cutter, and a pull-wire. The deflectable distal tip is hinged to a distal region of the catheter body at a hinge. The rotatable cutter is proximal to the deflectable distal tip. The pull-wire is mounted to the deflectable distal tip and extends proximally lateral to the cutter and hinge. The pull-wire is configured to be pulled proximally to deflect the deflectable distal tip.

This and other embodiments can include one or more of the following features. The atherectomy catheter can further include an optical fiber for OCT imaging coupled to the rotatable cutter. The optical fiber can be attached to the rotatable cutter but be otherwise free to float within the catheter body. The atherectomy catheter can further include a pull shaft extending within the catheter body and coupled to the pull-wire, and the pull shaft can be configured to pull the pull-wire proximally to deflect the distal tip. The pull-wire and pull shaft can be movable with respect to an outer shaft of the catheter body. The pull shaft can be concentric with the outer shaft. The atherectomy catheter can further include a drive shaft configured to rotate the rotatable cutter. The drive shaft can be hollow, and an optical fiber for OCT imaging can extend within the drive shaft. The pull-wire can be configured to deflect the distal tip without impacting the directionality of the catheter. The deflection of the distal tip can expose the cutter.

The present invention also relates to non-contact drive systems for driving catheter systems. For example, the catheter may include a magnetic response element that is configured to mate with a magnetic drive element that can be non-sterile and mounted outside of the sterile operating field to drive the catheter. The response element and the drive elements may be configured to provide magnetic gears that control the forward and backwards (e.g., clockwise and counterclockwise) rotation of the catheter shaft(s) and/or translation of the catheter shaft(s).

In general, in one aspect, a system for driving non-contact actuation of a shaft of a catheter includes a catheter and a driver. The catheter includes a shaft extending from a proximal end of the catheter to a distal end of the catheter and a magnetic response element attached to a proximal end of the shaft. The driver has a magnetic response element and is configured to receive the proximal end of the catheter. The magnetic response element and the magnetic drive element are configured to magnetically engage such that activation of the driver results in actuation of the shaft.

This and other embodiments can include one or more of the following features. The cutter can include a rotatable cutter. The shaft can be a drive shaft connected to the rotatable cutter. Activation of the driver can result in rotation of the drive shaft and rotation of the rotatable cutter. Activation of the driver can result in translation of the driveshaft and the rotatable cutter. The rotatable cutter can include an OCT sensor attached thereto. The shaft can be an outer shaft of the catheter. Activation of the driver can results in longitudinal translation of the outer shaft. Activation of the driver can result in rotation of the outer shaft. The response element can include magnets arranged circumferentially around a bearing, and the bearing can be attached to the shaft. The magnets can be arranged around the circumference in alternating polarities. The driver can include a rotor having magnets arranged circumferentially around the rotor. The driver can include a channel configured to hold the catheter such that the response element and driver element can engage.

In general, in one aspect, a system for driving non-contact actuation of a shaft of a catheter includes a catheter and a driver. The catheter includes a shaft extending from a proximal end of the catheter to a distal end of the catheter. The driver is configured to receive the proximal end of the catheter and actuate the shaft with a drive mechanism. The system is configured such that a sterile covering can be interposed between the drive mechanism and the shaft without preventing the driver from actuating the shaft.

This and other embodiments can include one or more of the following features. The cutter can include a rotatable cutter. The shaft can be a drive shaft connected to the rotatable cutter. Activation of the driver can result in rotation of the drive shaft and rotation of the rotatable cutter. Activation of the driver can result in translation of the driveshaft and the rotatable cutter. The rotatable cutter can include an OCT sensor attached thereto. The shaft can be an outer shaft of the catheter. Activation of the driver can result in longitudinal translation of the outer shaft. Activation of the driver can results in rotation of the outer shaft. The response element can include magnets arranged circumferentially around a bearing, and the bearing can be attached to the shaft. The magnets can be arranged around the circumference in alternating polarities. The drier can include a rotor having magnets arranged circumferentially around the rotor. The driver can include a channel configured to hold the catheter such that the response element and driver element can engage.

In general, in one aspect, a method of driving actuation of a shaft of a catheter includes: placing a sterile covering between a catheter and a driver; magnetically engaging a response element of the catheter with a drive element of the driver through the sterile covering; and activating the drive element such that a shaft of the catheter connected to the response element is actuated.

This and other embodiments can include one or more of the following features. Activating the drive element can include rotating the drive element such that the shaft is rotated. Activating the drive element can include longitudinally translating the drive element such that the shaft is longitudinally translated.

In general, in one aspect, a method of driving actuation of a shaft of a catheter includes: placing a sterile covering between a catheter and a driver; engaging a shaft of the catheter with a drive element of the driver through the sterile covering; and activating the drive element such that the shaft is actuated without contacting the drive element.

This and other embodiments can include one or more of the following features. Activating the drive element can include rotating the drive element such that the shaft is rotated. Activating the drive element can include longitudinally translating the drive element such that the shaft is longitudinally translated.

In general, in one aspect, a non-contact driver device to drive a shaft within a catheter includes a housing, a channel in the housing for receiving an end region of a catheter, and a magnetic drive element without the housing. The channel can be configured to be covered with a sterile drape so that the catheter does not directly contact the surface of the channel. The magnetic drive element can include a plurality of magnets or magnetizable elements configured to create a magnetic field within the channel and drive a magnetic response element within a catheter held in the channel.

This and other embodiments can include one or more of the following features. The plurality of magnets or magnetizable elements can be configured to create a rotating magnetic field to rotate the magnetic response element. The plurality of magnets or magnetizable elements can be configured to translate longitudinally to move the magnetic response element longitudinally. The magnetic channel can be a crevice configured such that the end region of the catheter can be placed on top of the crevice. The driver can further include a rotor having magnets arranged circumferentially around the rotor. The magnetic drive element can be configured to create a dynamic magnetic field within the channel to drive rotation of the magnetic response element.

BRIEF DESCRIPTION OF THE DRAWINGS

FIGS. 4A-4B show one variation of a magnetic (non-contact) driver configured to engage with a magnetic response element such as the one shown in FIGS. 1-3 to drive rotation of the catheter shaft;

FIGS. 6A-6B show the outer housing of the driver of FIGS. 4A-4B.

FIG. 13 shows distal response element and drive element of the system of FIGS. 10A-10B.

FIGS. 14A-14E show an exemplary atherectomy catheter having a pull-wire activation mechanism for deflection of the distal tip.

FIGS. 15A-15B show transparent and cross-sectional views of the atherectomy catheter of FIGS. 14A-14B;

FIGS. 20A-20K illustrate an exemplary atherectomy catheter that can be used with the non-contact drive systems or pull-wire mechanisms described herein.

FIGS. 21A-21I illustrate an exemplary guide wire placement catheter that could be used with the non-contact drive systems or pull-wire mechanisms described herein.

DETAILED DESCRIPTION

Non-Contact Control of Actuation of a Catheter

The non-contact catheter drive systems described herein include a magnetic driver having one or more drive elements that can be kept separate from the catheter to interact magnetically with a response element that is part of or attached to the catheter. The magnetic driver magnetically engages the catheter response element to actuate elements of the catheter without directly contacting the catheter or the catheter handle. Because this system allows non-contact control of the catheter (e.g., rotation of a drive shaft in the catheter), the sterile filed surrounding a patient may be kept intact even when using a non-sterile magnetic driver. For example, the magnetic driver can be covered in a sterile covering (e.g., a bag or sheet) that can be kept intact (not ripped or subject to tearing) while still engaging the catheter to drive actuation, such as rotation, steering, or lateral movement, of one or more elements of the catheter.

In general, a non-contact catheter driver may include one or more drive elements that can cause a moving magnetic field of sufficient strength to drive movement of a magnetic response element in a catheter that is placed (e.g., secured) within a channel of the non-contract catheter driver. A sterile drape or the like may be paced between the non-contract catheter driver and the catheter that it is driving; the drape does not interfere with the activity of the driver and the driver does not need to break the sterile field (e.g., drape) to operate on the catheter.

Figure 1:
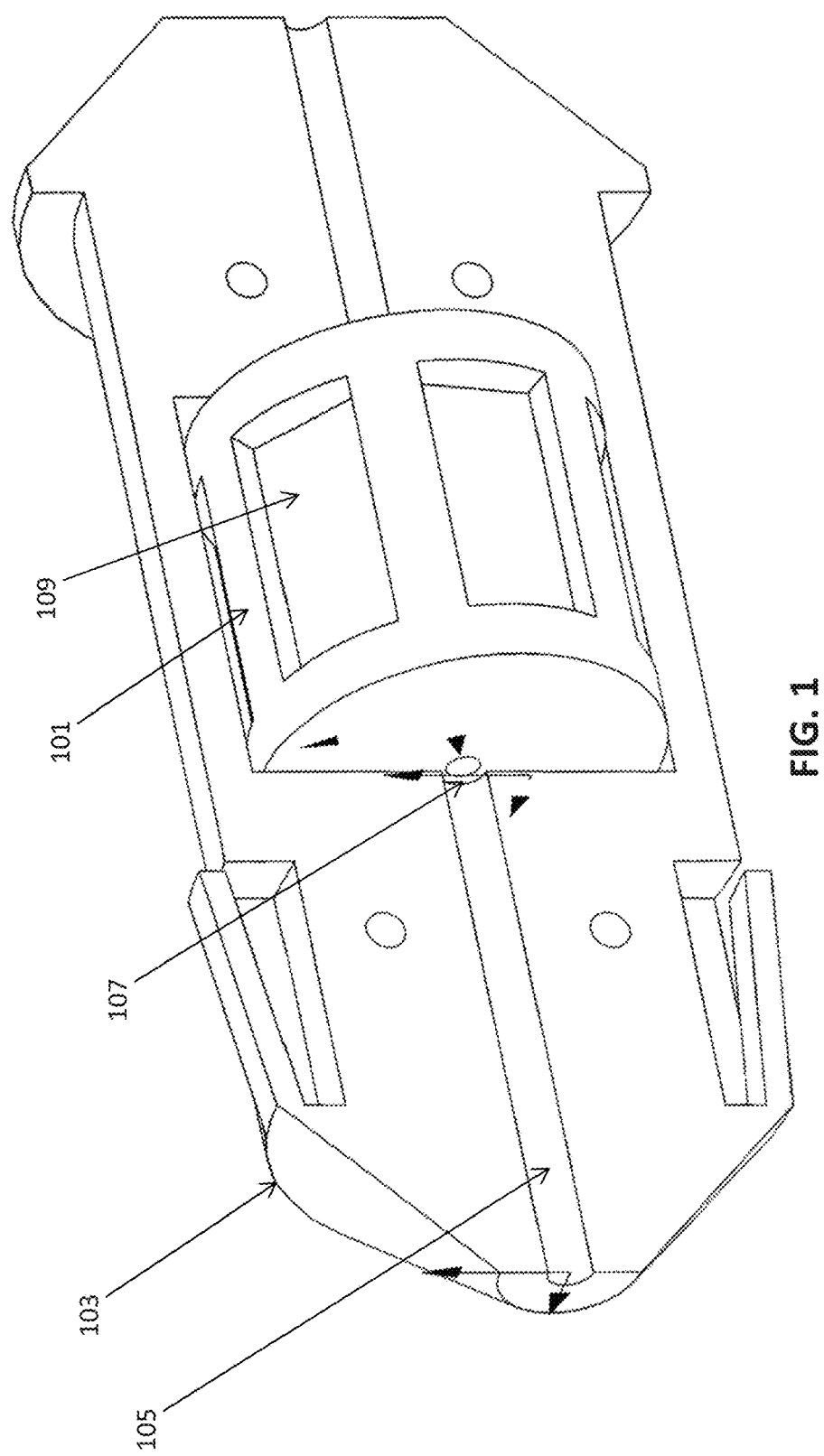
FIG. 1 shows one variation of a magnetic response element that can be attached to a shaft of a catheter for rotating the shaft.
Figure 2:
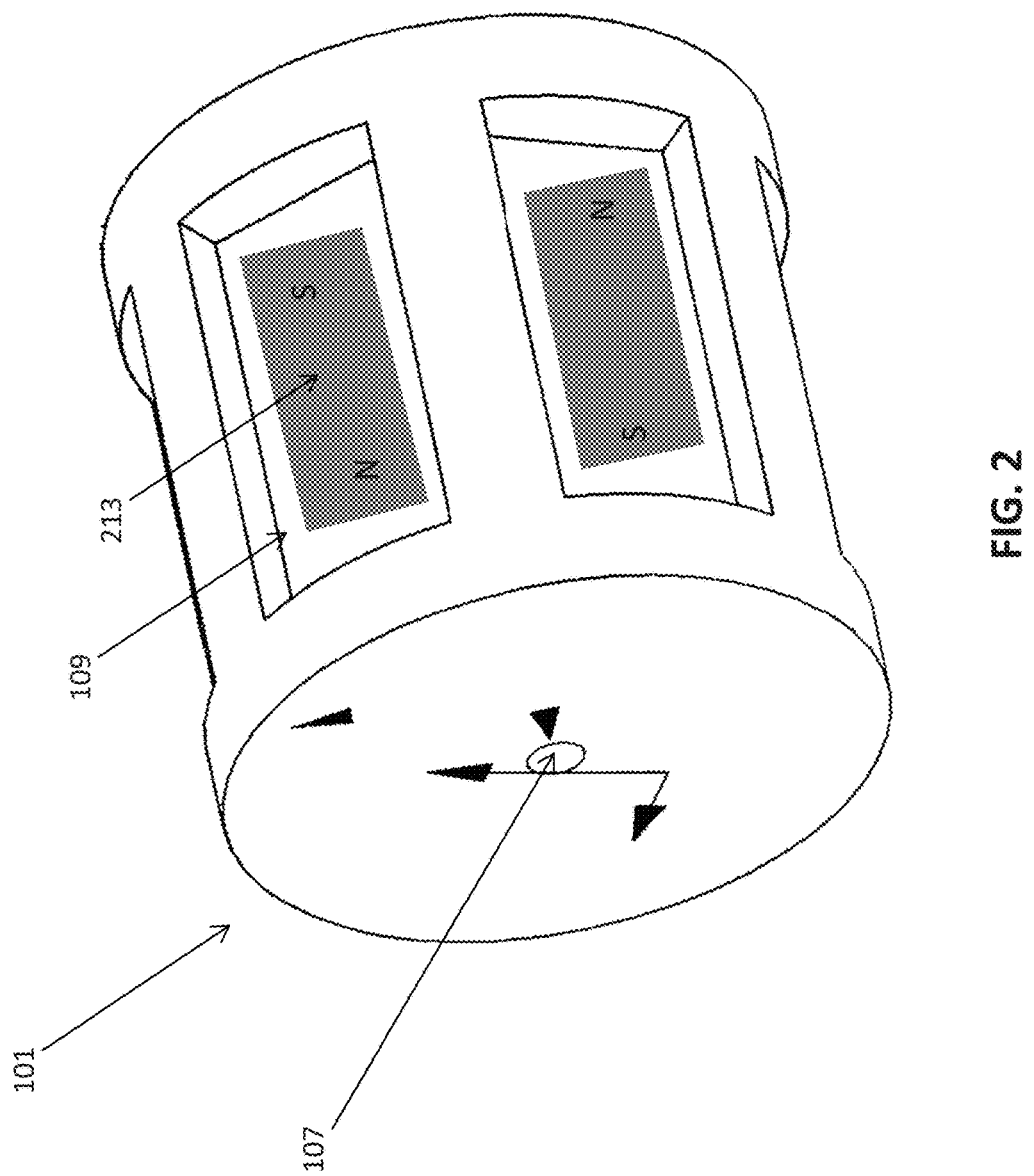
FIG. 2 shows a close-up of the bearing of the magnetic response element of FIG. 1.
Figure 3:
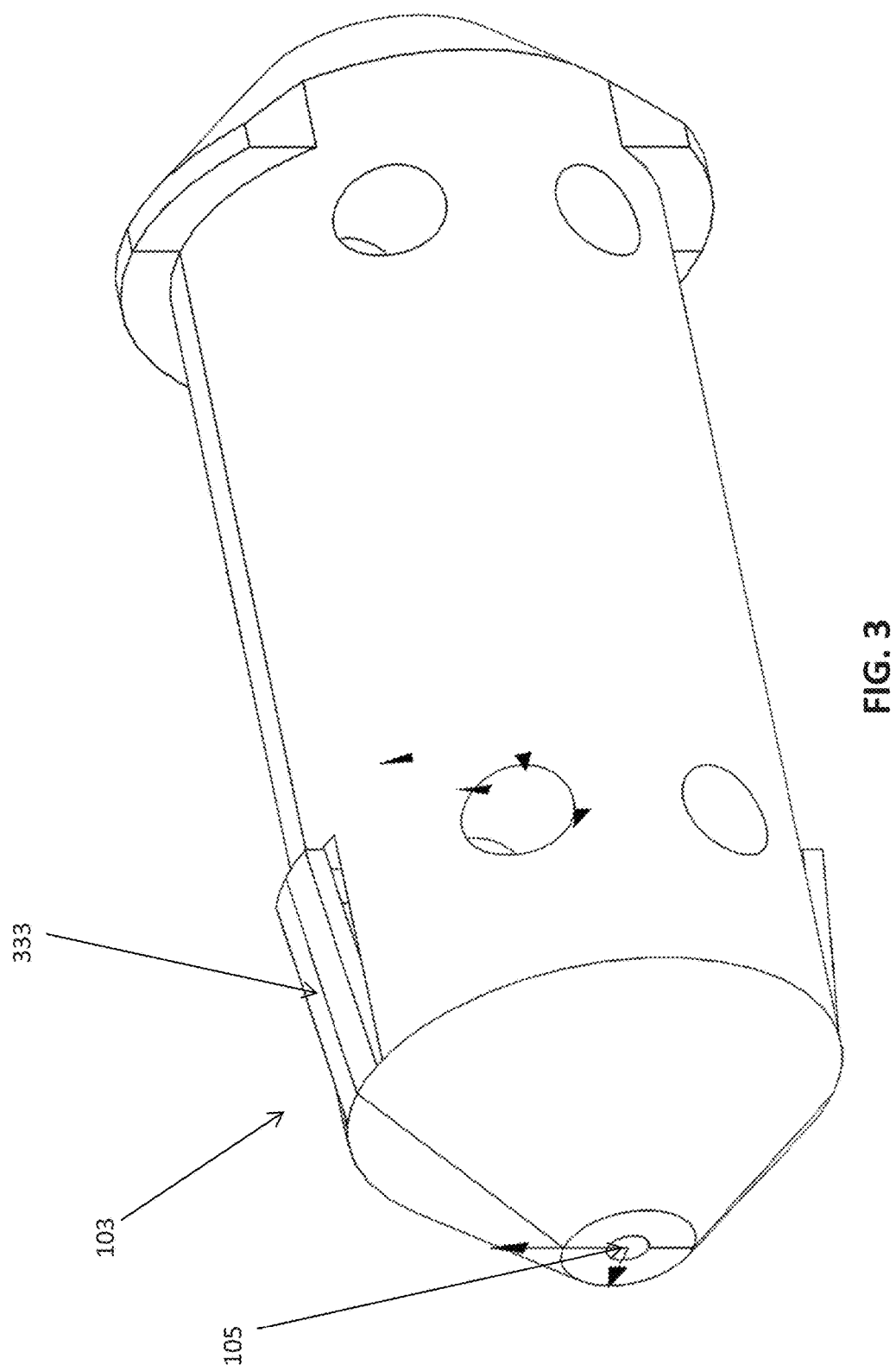
FIG. 3 shows the outer housing of the magnetic response element of FIG. 1

FIGS. 1-3 illustrate one variation of a magnetic response element that can be coupled to a rotatable drive shaft within a catheter. Referring to FIG. 1, a magnetic response element 100 can include a housing 103 having a channel 105 therethrough for engagement with a driveshaft of a catheter. The response element 100 can further include a central magnetic bearing 101. The bearing 101 can include a bearing channel 107 configured to fixedly attach to a driveshaft of the catheter (e.g. through glue, etc.). The bearing 101 can rotate within the housing 103, thus causing the catheter driveshaft to rotate as well (the driveshaft will rotate with the bearing 101 and relative to the housing 103).

The bearing 101 can include a set of magnetic holders 109, such as pockets in the bearing 101, configured to hold magnetic domains of opposite polarity (i.e., N, S, N, S). There can be, for example 1-20 magnetic holders 109 arranged around the circumference of the bearing 101. A simple arrangement of a six holders 109 around the circumference of the bearing 101, each holder 109 with a single magnet 213, is shown in FIG. 2. In other embodiments, two or more magnets can be arranged per holder. As described further below, the magnetic domains can interact with a magnetic driver to drive rotation of the catheter shaft.

In some embodiments, there can be multiple magnetic response elements 100 for use with a single catheter to drive different shafts within the catheter (for example, to drive rotation of a cutting element and rotation of the cutter).

Further, in some embodiments, there can be multiple magnetic response elements 100 arranged in series and fixed to a single driveshaft. In one configuration, each response element 100 in the series can include a different number or arrangements of magnetic domains or magnets 213 therein, such that the shaft can be configured to counter-rotate and/or rotate at different speeds. In another configuration, each response element 100 of the series can have the same arrangement of magnetic domains or magnets 213 there, but the series alignment can advantageously provide more torque for rotating the driveshaft.

As shown in FIG. 3, the housing 103 having a channel 105 therethrough for engagement with a driveshaft of a catheter. The housing 103 can further include a locking mechanism, such as a snap lock 333 configured to keep the housing 103 from sliding within the driver once mounted.

FIGS. 4A-6B illustrate one variation of a magnetic driver that may be mounted or held and which may engage the magnetic response element to drive rotation of the drive shaft in the device. The driver can secure the catheter within the sterile field.

Figure 4A:
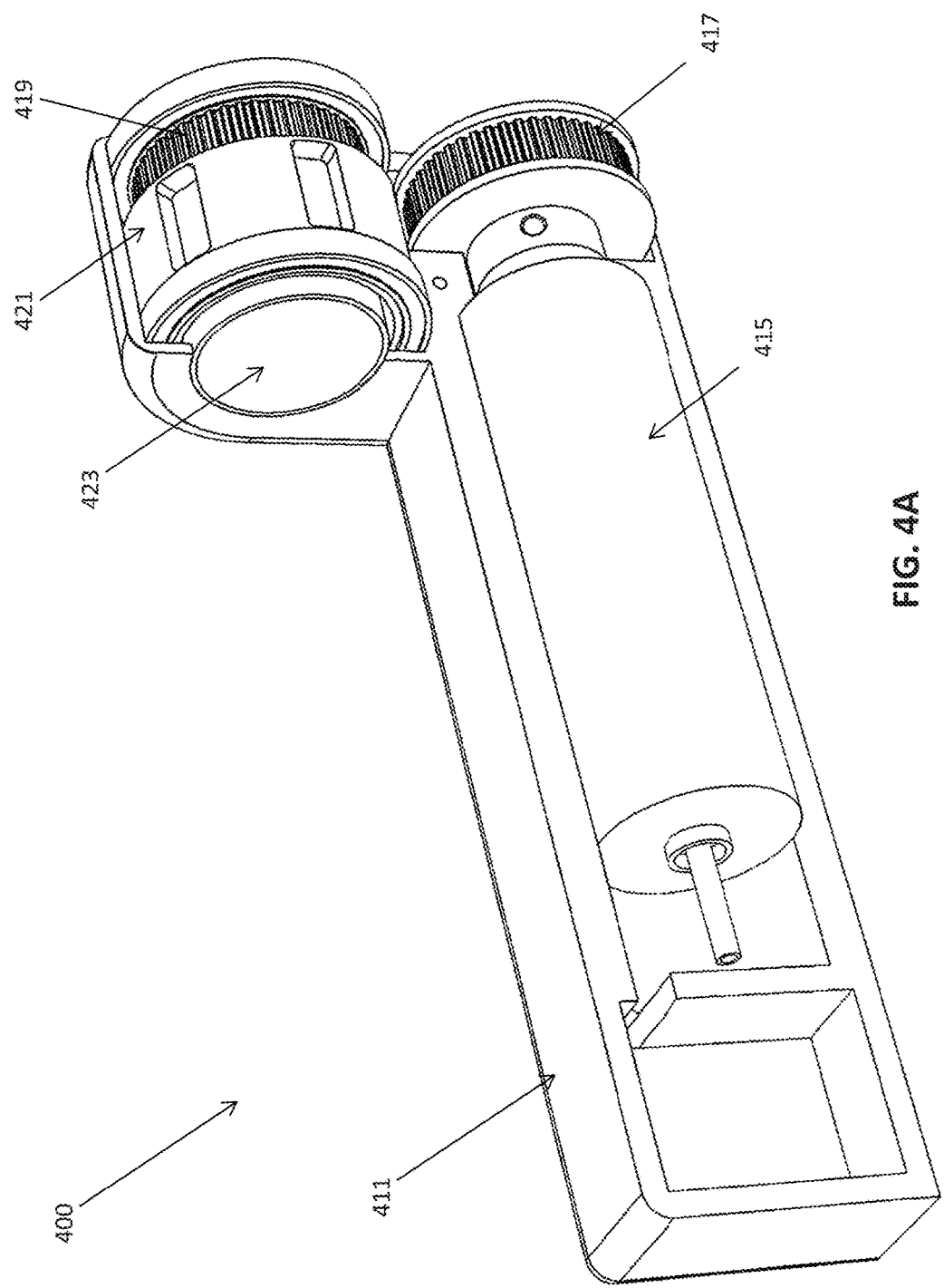

Referring to FIGS. 4A-4B, a magnetic driver 400 includes a housing 411 having a connector 423, such as a cylindrical channel or opening, for engagement with a response element, such as response element 100. The connector 432 can include a mechanism configured to interlock with the locking mechanism on the housing 103 of the response element 100, such as to interact with the snap lock 333.

The magnetic driver 400 can further include a motor 415 connected to a first gear 417. The first gear 417 can be engaged with a second gear 419 through a belt 525 (see FIG. 5). The second gear 419 can be connected to a drive rotor 421. The drive rotor 421 can include magnetic holders 409, such as pockets in the rotor 421, configured to hold magnetic domains.

Figure 5:
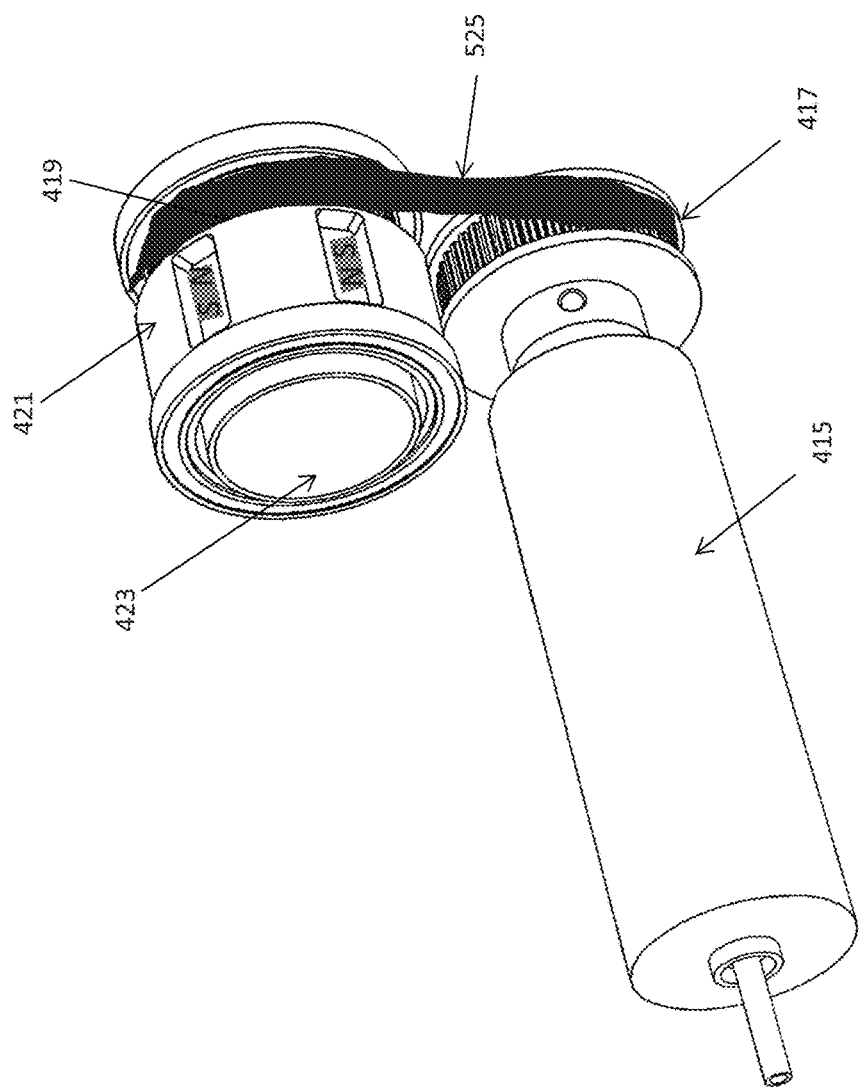
FIG. 5 shows the pulley system used to drive the gears and thus the rotor of the driver of FIGS. 4A-4B.

The holders 409 and/or the magnetic domains in the pockets can be configured so as to align with (but of opposite polarity to) the holders 109 and domains of the response element, such as response element 100. Thus, for example, there can be six holders 409, each with a single magnet 513, as shown in FIG. 5.

Figure 6A:
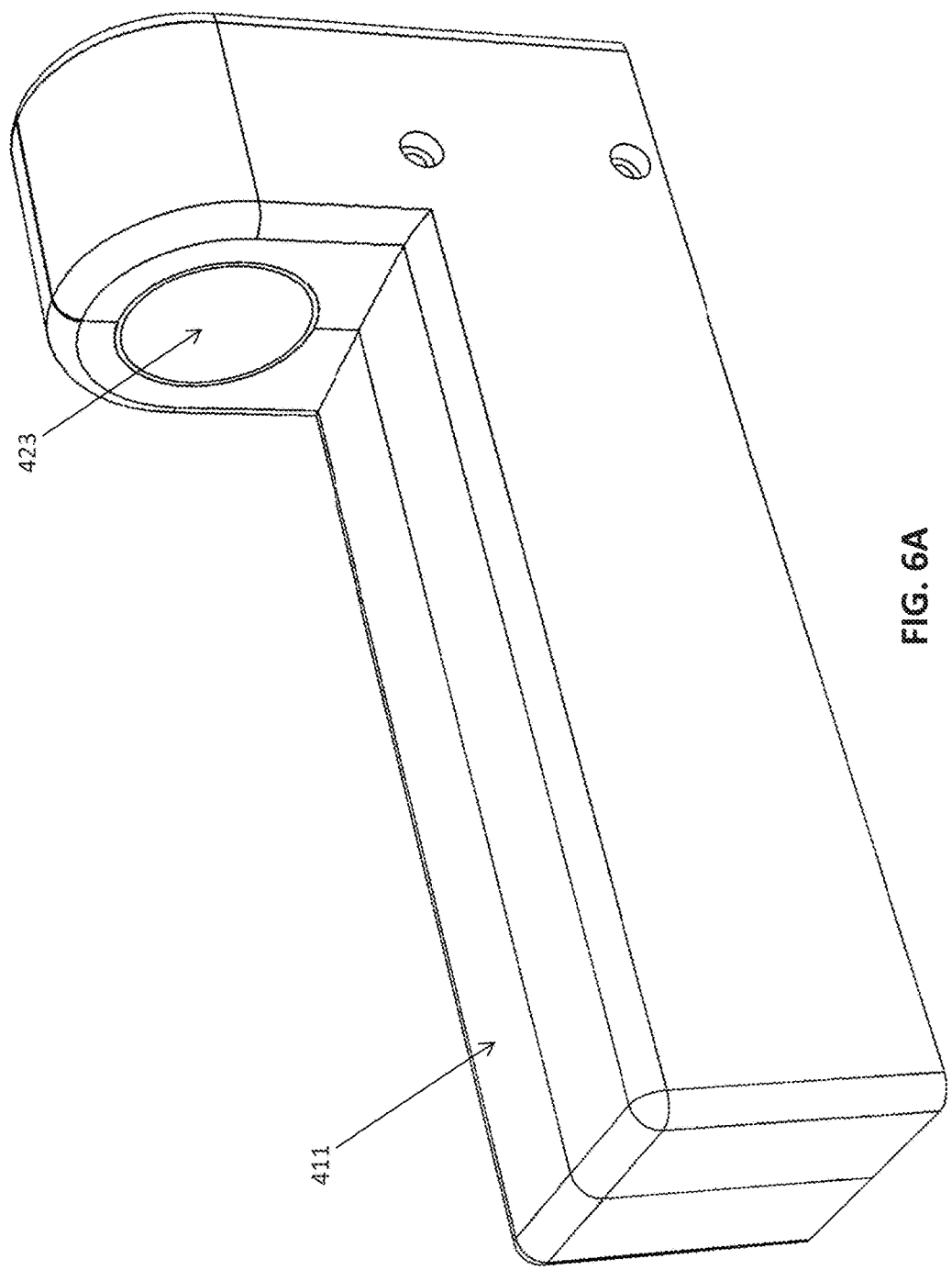

As shown in FIGS. 6A-6B, the housing 411 includes a connector 423 for engagement with the response element 100. The connector 423 can be a hollow channel, which can have an uninterrupted sealed interior.

The magnetic driver 400 can be used to drive rotation of a catheter having a response element, such as response element 100. In one embodiment, the housing 103 of response element 100 can be configured to slide into the opening of the connector 423. As the housing slides in, the magnetic domain of the response element 100 can align with the magnetic domain of the driver. For example, the magnets 513 shown in FIG. 5 can align with the magnets 213 shown in FIG. 2. As such, when the motor 415 is activated, it can turn the first gear 417, which will activate the belt 525, turning the second gear 419 and thus the rotor 421. Due to the interaction between the magnets 513 on the rotor 421 and the magnets 213 on the bearing 101, the bearing 101 will rotate, thus causing the driveshaft connected thereto to rotate in the same clockwise/counterclockwise direction as the gears 417, 419. Such rotation of the driveshaft can thus provide for cutting, imaging, etc. of a catheter. Thus, while the catheter and housing 103 of the response element 100 remain static, the driveshaft can be rotated by the interaction between the magnetic domains.

Advantageously, by using this non-contact drive system, the catheter can remain sterile while the magnetic driver 400 can be in the non-sterile field. For example, a sterile bag or sheet can be placed over the housing 101 or lined within the connector 423 to avoid direct contact between the catheter and the magnetic drive 400.

Although the response element 100 is described above for use with a driveshaft of a catheter, it can likewise be used for any shaft of a catheter, such as an outer torque shaft.

Figure 7:
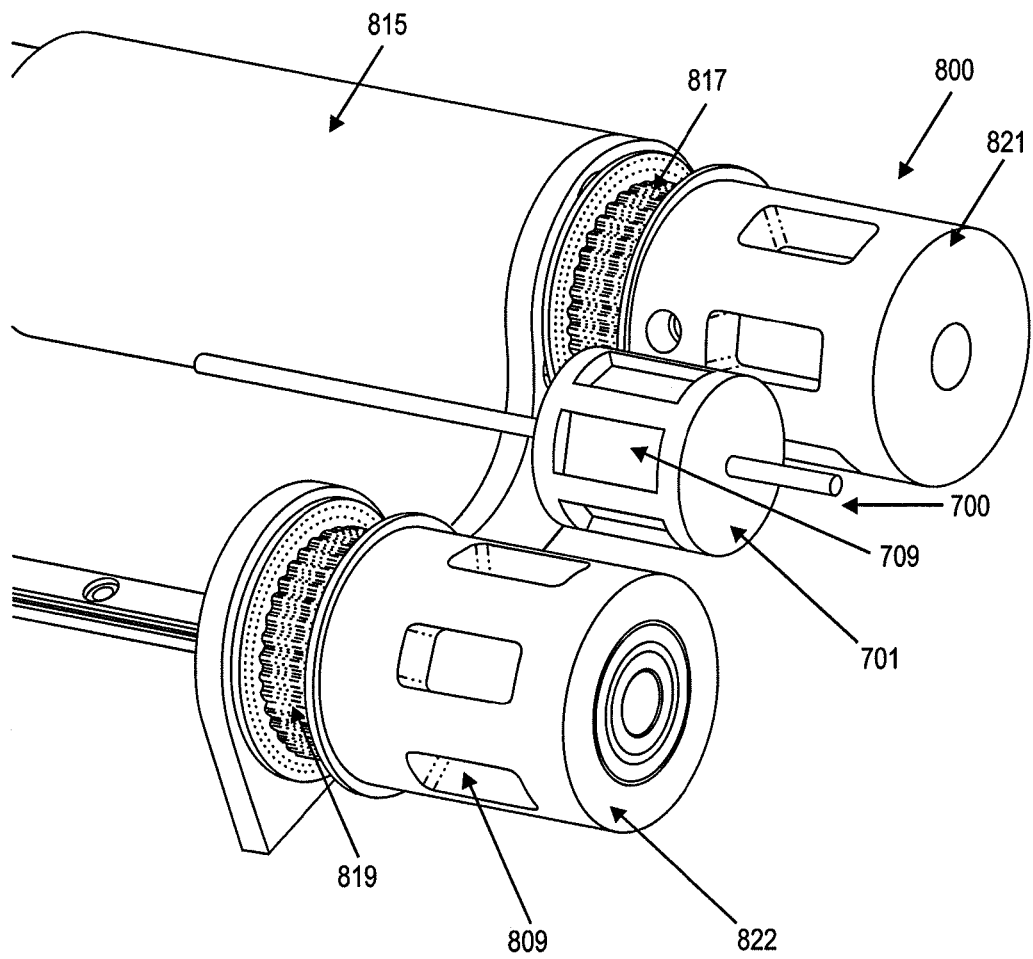
FIG. 7 shows another variation of a system for magnetic, non-contact rotation of a shaft of a catheter.
Figure 8:
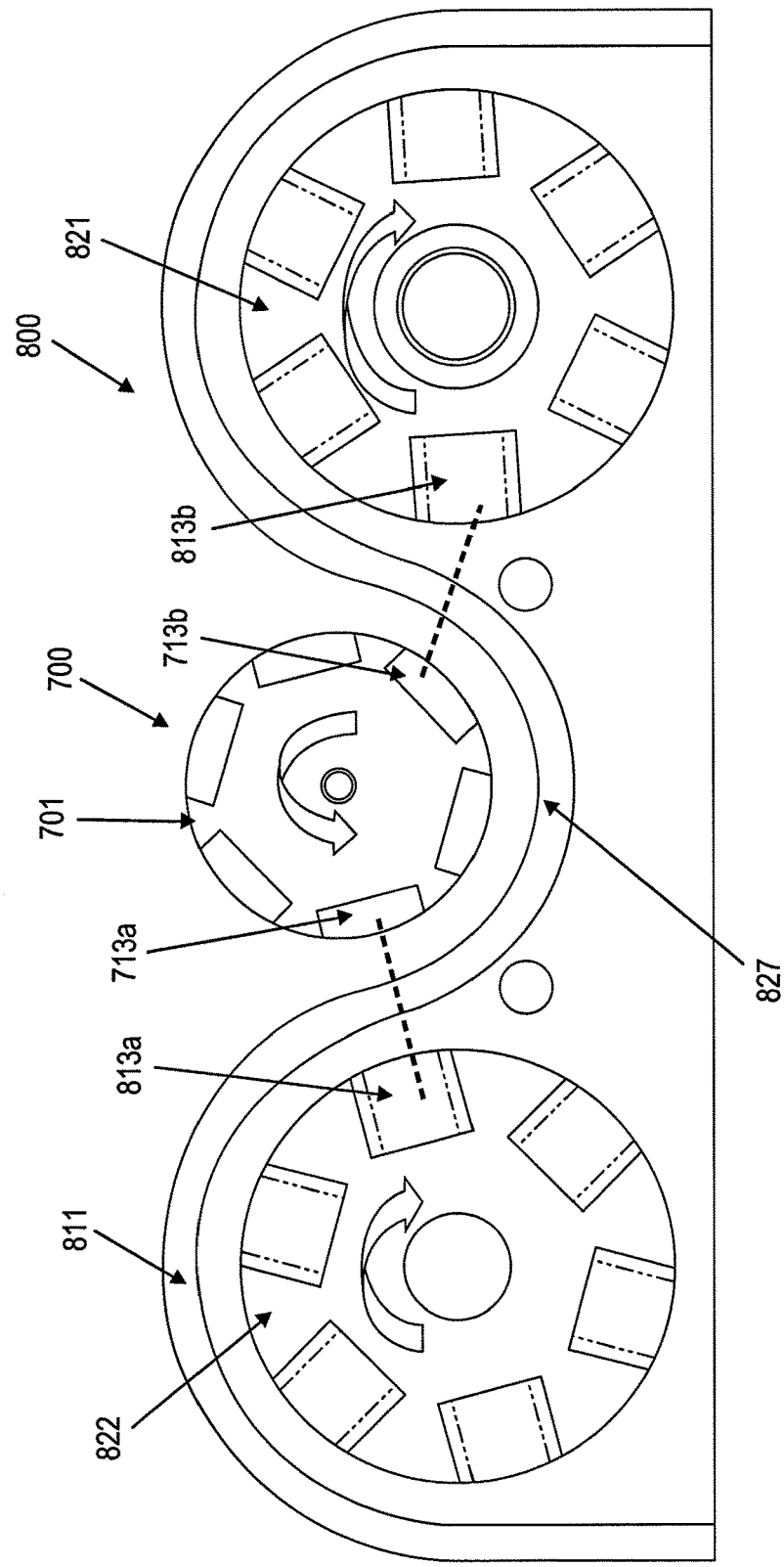
FIG. 8 is a cross-section of the system of FIG. 7.

FIGS. 7-8 illustrate another variation of a non-contact system including a response element and a driver that can impart rotational motion into a shaft of a catheter, such as a drive shaft or torque shaft. The response element 700 can be configured similarly to the response element 100. It can thus include a bearing 701 having a bearing channel 707 configured to fixedly attach to a shaft of the catheter. The bearing 701 can include a set of magnetic holders 709, such as pockets in the bearing 701, configured to hold magnetic domains of opposite polarity, such as single magnets 713 (see FIG. 8).

The magnetic driver 800 can include a motor 815 connected to a first gear 817. The first gear 817 can be engaged with a second gear 819 through a belt extending between the gears 817, 819. In this embodiment, the first gear 817 can be connected to a first rotor 821 while the second gear 819 can be connected to a second rotor 822. Each of the rotors 821, 822 can include magnetic holders 809, such as pockets in the rotors 821,822, configured to hold magnetic domains. The holders 809 and/or the magnetic domains in the holders can be configured so as to align with (but of opposite polarity to) the holders 709 and domains of the response element 700. Thus, each rotor 821, 822 contain magnets 813 (see FIG. 8) mounted with polarity opposite that of the adjacent magnet on the same rotor so as to create an alternating magnetic field. This may ensure proper "meshing" and alignment of the virtual magnetic gearing of the response element and driver. The magnetic driver 800 can be contained within a housing 811 (see FIG. 8) having a crevice or channel 827 configured to hold the response element 700, i.e., to allow the response element 700 to rest therein.

The magnetic driver 800 can be used to drive rotation of the shaft of the catheter to which the response element 700 is attached. To do so, the response element 700 (connected to the shaft of the catheter) can be placed in the channel 827. The response element 700 will thus sit between the first and second rotors 821,822. When the motor 715 is activated, it will turn the first gear 717, which will activate the belt and thus turn the second gear 719. As the gears 717, 719 turn, the rotors 821, 822 will turn. The rotation of the rotors 821, 822 will cause the bearing 701 to rotate in the opposite direction (e.g. clockwise if the rotors 821, 822 are rotating counterclockwise) due to the interaction between the domains on the bearing 701 and the domains on the rotors 821.

For example, as shown in FIG. 8, the magnet 713a will interact with the magnet 813a. As the rotor 821 spins clockwise, the attraction between the two magnets 713a, 813b will cause the bearing 701 to spin counterclockwise. As it does so, the magnets 713b and 813b will come closer together, thereby causing the attraction between those magnets 713b, 813b to continue the counterclockwise spin of the bearing 701. Continuous interaction between the magnets 813 of the clockwise-rotating rotors 821, 822 and the magnets 713 of the bearing 701 will thus cause the bearing 700 to continue to rotate counterclockwise.

In one embodiment, the rotors 821, 822 are aligned such that the holders 709 in each respective rotor 821,822 are slightly offset from one another (as best seen in FIG. 8). This offset can advantageously provide a smoother rotation of the bearing 701 by allowing the magnets 713 thereon to interact with a magnet 813 of the first rotor 822, followed by interaction with a magnet 813 of the first rotor 821, etc. Such back-and-form transitioning between the magnets of the first and second rotors 811, 822 avoids having a slowing or jolting of the bearing 701 rotation that might otherwise occur if magnets 813 of both rotors 821, 822 interacted and then disengaged simultaneously.

The response element 700 driver 800 can advantageously allow non-contact actuation of a driveshaft of a catheter. As a result, the catheter can be actuated while maintaining a sterile field. For example, a sterile bag or sheet can be placed over the housing 811 and/or such that it lines the channel 827 to separate the sterile and non-sterile field. Because the catheter with the response element 700 can simply be placed on top of the housing 811 to actuate the driveshaft, the system provides easier sterility options than those where snapping or physical connection of the catheter and the driver are required.

Figure 9:
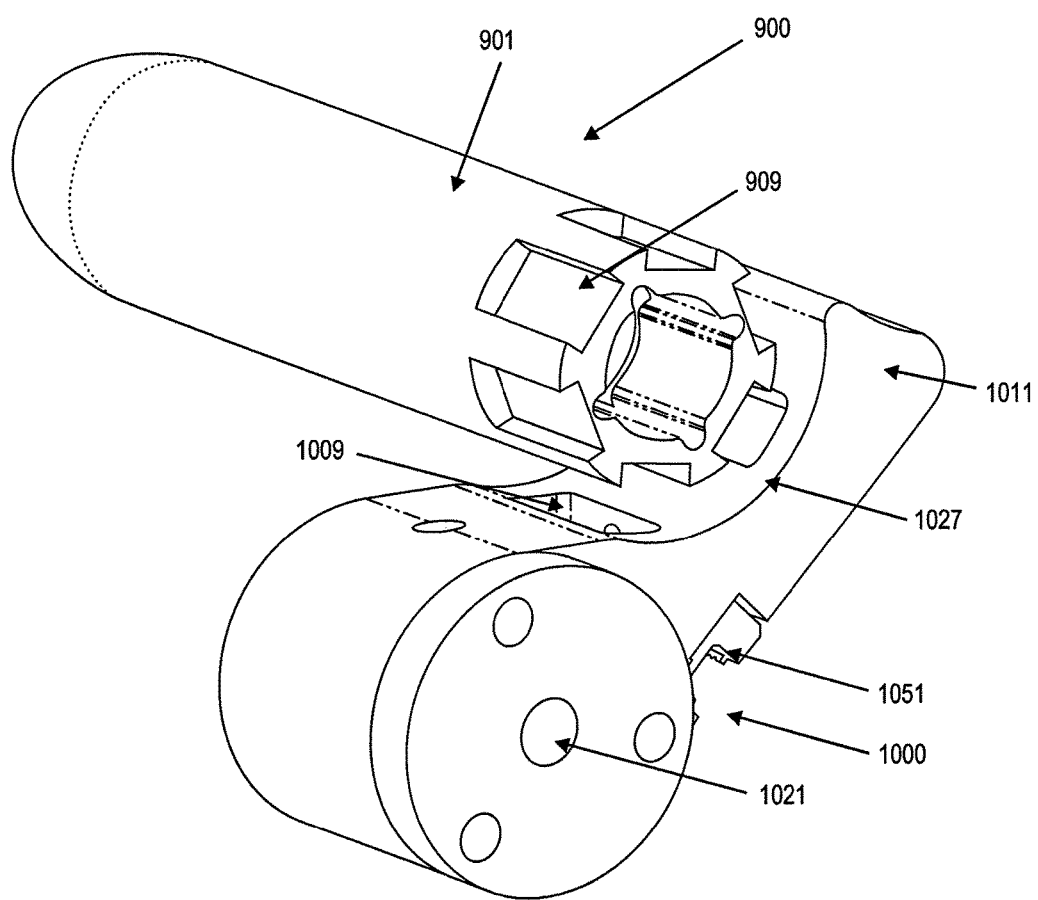
FIG. 9 shows a variation of a system for magnetic, non-contact translation of a shaft of a catheter.

FIG. 9 illustrates a variation of a non-contact system including a response element and a driver that can be used to impart translational linear motion into a component of a catheter. The response element 900 can include a bearing 901 configured to fixedly attach to an outer shaft or torque shaft of the catheter. The bearing 901 can include a set of magnetic holders 909, such as pockets in the bearing 901, configured to hold magnets therein. In one embodiment, the bearing 901 can be configured to only translate (not to rotate). As a result, the holders 909 can include domains or magnets of the same polarity. The magnetic holders 909 can extend around the circumference of the bearing 901 such that the bearing 901 can engaged with the driver 1000 regardless of the direction in which it is set down on the driver 1000.

The magnetic driver 1000 can be contained within a housing 1011 having a crevice or channel 1027 configured to hold the response element 900, i.e., to allow the response element 900 to rest therein. The channel 1027 can include magnetic holders 1009 therearound, such as a pocket in the driver 1000, configured to hold magnetic domains. The holders 1009 and/or magnetic domains in the holders can be configured to align with (but of opposite polarity to) the holders 909 and domains of the response element 900.

The magnetic driver 1000 can be configured to slide along a slide bearing plate via attachments 1051. The magnetic driver 1000 can further include a connector 1021 configured to connect to a motor for translating the driver 1000. For example, the connector 1021 can connect to a threaded rod attached to a rotary motor such that rotation of the motor imparts translation of the driver 1000.

The magnetic driver 1000 can be used to drive linear translational motion of the torque shaft attached to the response element 900. To do so, the response element 900 (connected to a torque shaft of the catheter) can be placed in the channel 1027. As the driver 1000 is moved linearly, the interaction between the magnetic domains on the driver 1000 and the magnetic domains on the response element 900 will cause the response element 900, and thus the attached torque shaft, to move linearly as well. As a result, the torque shaft can be driven forward (distally) or backwards (proximally). Such distal or proximal motion can be used, for example, to open a nosecone of an atherectomy device and/or pack tissue into the nosecone during an atherectomy procedure.

Although the response element 900 and driver 1000 have been described as imparting linear motion to a torque shaft of a catheter, it could be used to impart linear motion to other shafts of a catheter, such as a drive shaft attached to a cutter.

Advantageously, the response element 900 and driver 1000 can allow for non-contact linear actuation of a driveshaft of a catheter. As a result, the catheter can be actuated while maintaining a sterile field. For example, a sterile bag or sheet can be placed over the housing 1011 and/or such that it lines the channel 1027 to separate the sterile and non-sterile field. Because the catheter with the response element 800 can simply be placed on top of the housing 1011 to actuate the driveshaft, the system provides easier sterility options than those where snapping or physical connection of the catheter and the driver are required.

In some embodiments, a drive system can be used to impart both linear and rotational motion into an element or multiple elements of a catheter. For example, a system can include a combination of response elements and drive elements on one or more shafts of the catheter. Referring to FIGS. 10A-13, a drive system 1300 can include a magnetic response element 1100a and a driver 1200a to impart rotational and linear translational motion to an outer torque shaft of a catheter and a response element 1100b and driver 1200b to impart rotational motion to a driveshaft of the catheter.

Figure 11:
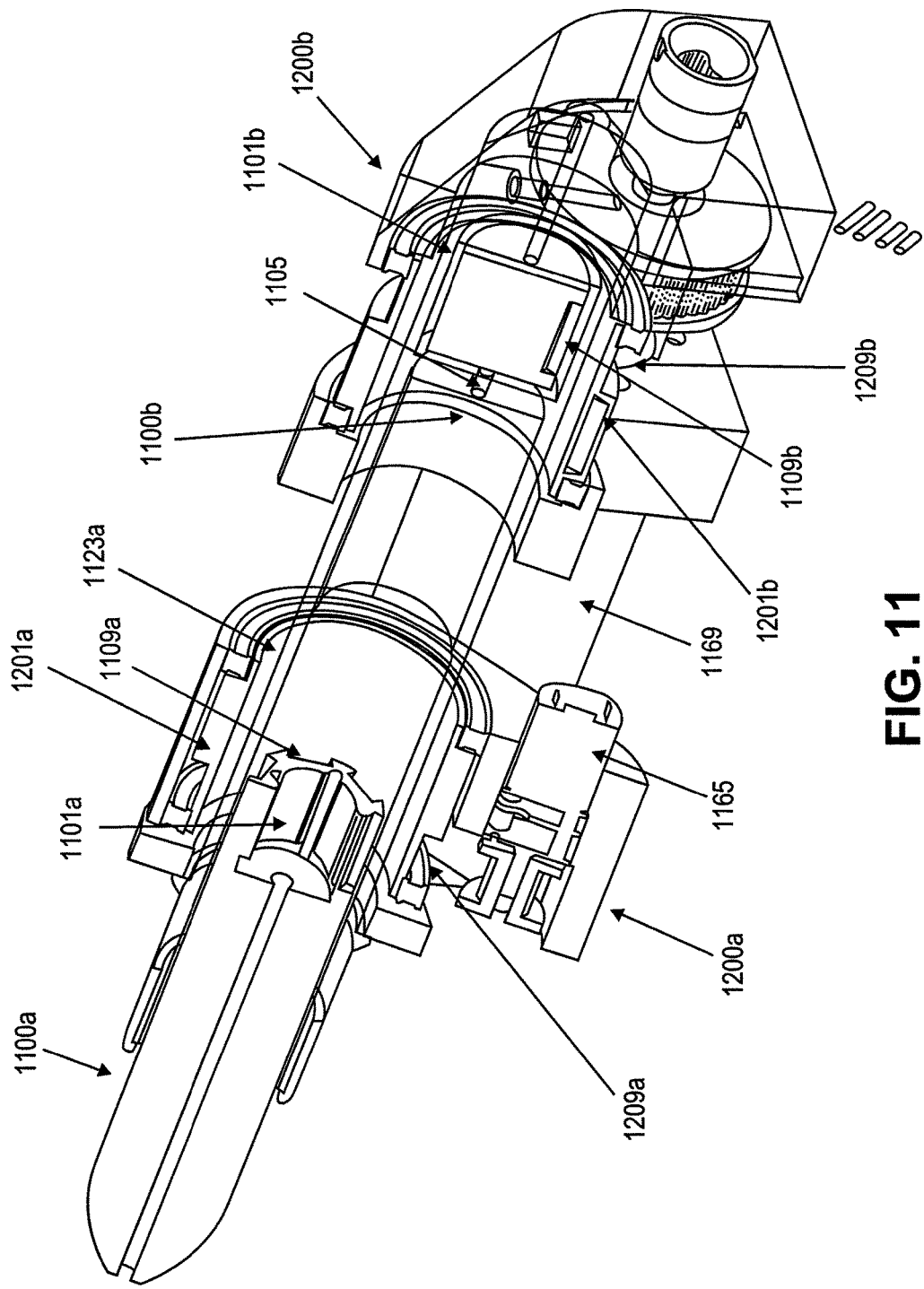
FIG. 11 is a horizontal cut away view of FIGS. 10A-10B.

Referring to FIG. 11, a first magnetic response element 1100a, similar to the response element 900, can include a bearing 1101a configured to fixedly attach to a torque shaft of the catheter. The bearing 1101a can include a set of magnetic holders 1109a, such as pockets in the shaft 1101a, configured to hold magnets therein. The magnetic domains can be arranged in domains of opposite polarity, i.e. neighboring magnets around the circumference can have opposite polarities.

Figure 12:
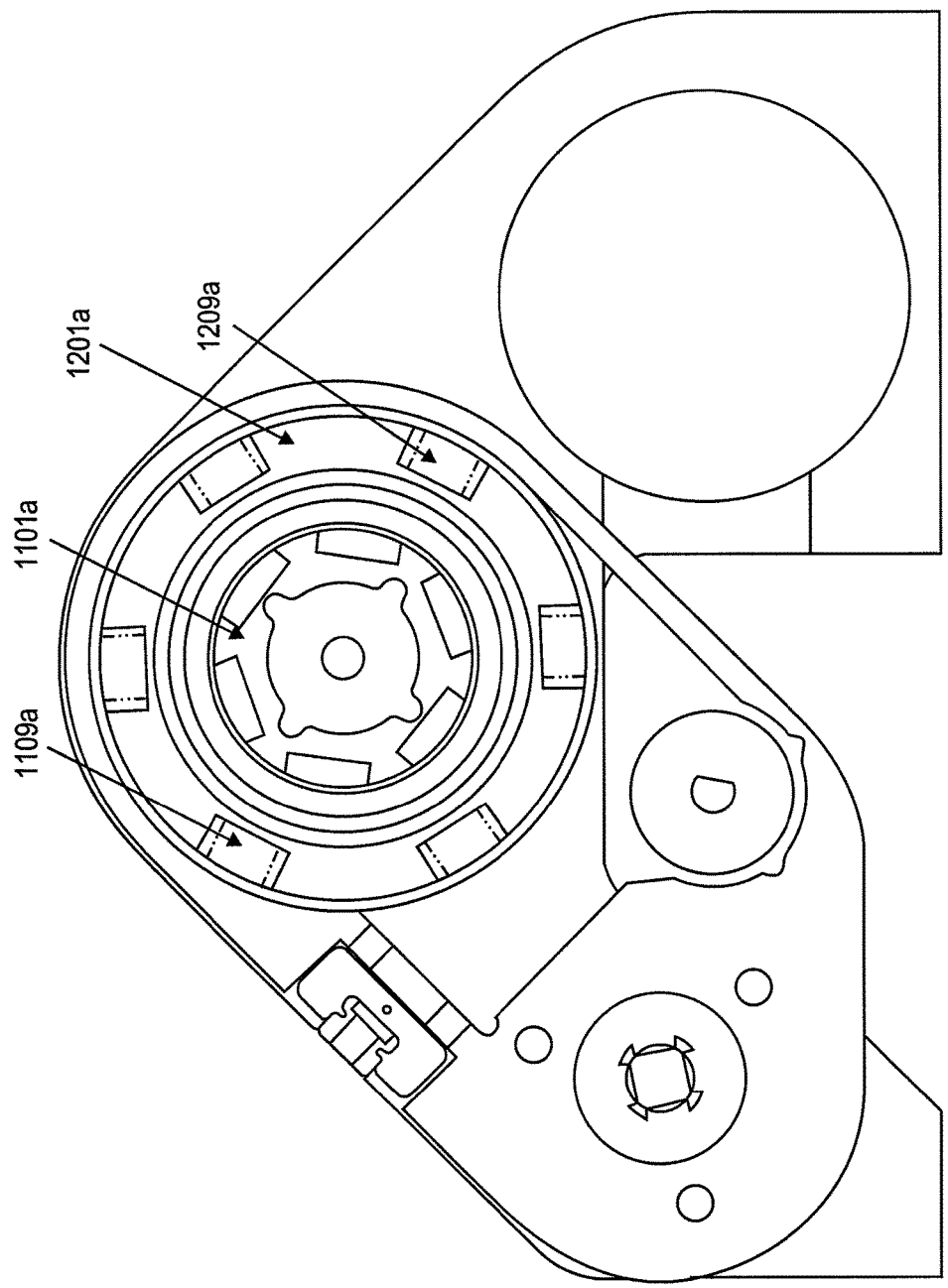
FIG. 12 shows a cross section of the distal response element and drive element of the system of FIGS. 10A-10B.

As seen best in FIGS. 12 and 13, the driver 1200a can include a rotor 1201a connected to a motor 1165 for translating the rotor 1201a as well as a motor 1167 to drive rotation of the rotor 1201a. The rotor 1201a can include magnetic holders 1209a, such as pockets in the rotor 1201a, configured to hold magnetic domains. The holders 1209a and/or the magnetic domains in the pockets can be configured so as to align with (but of opposite polarity to) the holders 1109a on the first magnetic response element 1100a. Similar to the driver 400 of FIGS. 4A-6B, the driver 1200a can be configured to actuate a shaft of a catheter having the response element 1101a by snapping the response element 1101a into a connector 1123 in a housing 111 of the driver 1200a to align the rotor 1201a around the magnets of the response element 1101a.

Figure 10A:
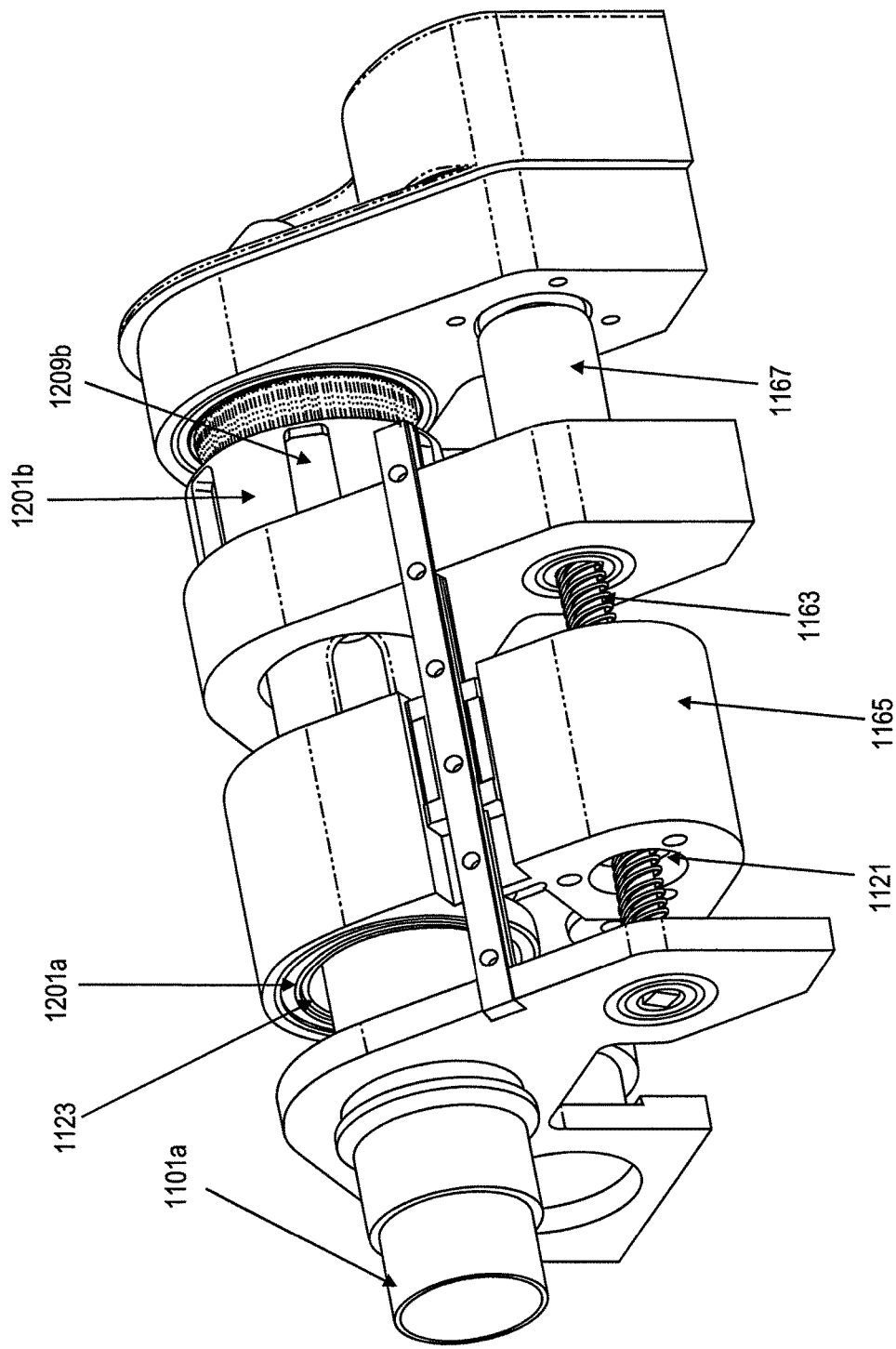
FIGS. 10A-10B show a variation of a system for magnetic, non-contact actuation of a catheter, including translation and rotation of a torque shaft and rotation of a driveshaft.
Figure 10B:
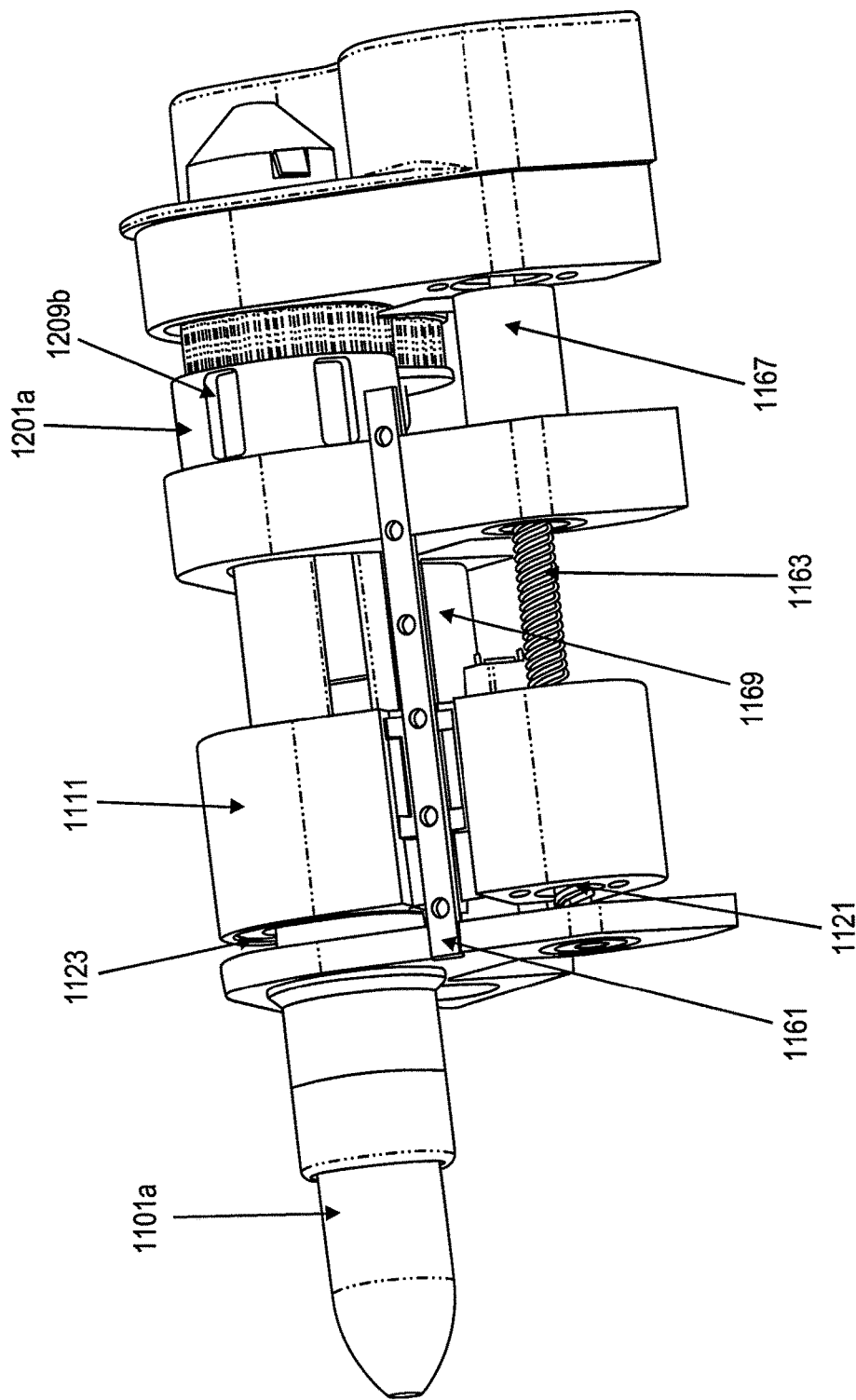

Rotation of the rotor 1201a (via motor 1167) will thus cause rotation of the response element 1101a, and thus the attached catheter shaft, such as a torque shaft, due to interaction between the magnets on the rotor 1201a and the response element 1101a. Further, translation of the rotor 1201 (via motor 1165 and a threaded rod 1163 extending through a connector 1121) will cause the response element, and thus the torque shaft, to translate linearly. As shown in FIGS. 10A and 10B, the sliding motion will thus cause the bearing 1101a of the response element 1100a to telescope in and out. In one embodiment, the driver can be used with an atherectomy catheter. Rotation of the driveshaft element can rotate the cutter and/or an imaging element of the atherectomy catheter. Rotation of the torque shaft of the atherectomy catheter can direct or orient the catheter and translation of the torque shaft relative to the drive shaft can deflect a distal end of the atherectomy catheter to expose the cutter.

Referring again to FIG. 11, a second response element 1100b can similarly include a bearing 1101b having magnetic domains 1109b therearound. The response element 1100b can include a 1105 therethrough for engagement with a driveshaft of a catheter. Further, a second drive element 1200b can include a rotor 1201b and magnetic holders 1209b. The response element 1100b can be configured to slide into the rotor 1201b such that the magnets of the response element 1100b and the rotor 1201b align. Accordingly, rotation of the rotor 1200b by the motor 1169 will cause the rotor 1201b, and thus the response element 1100b and attached driveshaft to rotate. In one embodiment, this rotation of the driveshaft can cause a distal cutter attached to the distal end of the driveshaft to rotate.

In some embodiments, the amount of possible "pull" force applied by the driver can be adjusted by the strengths of the magnets. The amount of force transmissible in both the rotational and translational motions can also be limited by the strength and arrangement of the magnets.

In some embodiments, a controller can be used to control the drivers described herein.

Atherectomy Catheter with Pull-Wire Activation Mechanism

An atherectomy catheter having a displaceable distal tip may include a lateral and/or external actuation element configured as a tendon, wire, rod, fiber, member, or the like that is generally attached to the distal tip of the catheter (though it may be hinged) and movable relative to the proximal portion of the catheter so that it can be moved (pushed or pulled) to actuate or displace the distal tip and expose the cutter of the atherectomy device. In some variations, this may be referred to as a pull-wire activation mechanism. The proximal end of the pull-wire may be attached to a pull shaft that extends all or partially down the length of the catheter from near the distal cutter toward the proximal handle. In some embodiments, the pull-wire extends proximally down the length of the catheter.

For example, in one embodiment, an atherectomy device includes a pull-wire activation mechanism. As should be apparent, a "pull-wire" lateral actuation element may be a tendon, wire, rod, member, or the like, and is not limited to wires. Although the actuation element may be referred to herein as a pull-wire, it should be understood that other structures may be used.

One example of an atherectomy device 1400 with an internal pull shaft 1402 and pull-wire 1524 is illustrated in FIGS. 14A-15B. The pull-wire is laterally displaced on the body of the catheter and spans the hinged region between the distal tip (nosecone region) and the rest of the catheter body. The atherectomy catheter 1400 can include a catheter body 1404, a cutter 1406 at a distal end of the catheter body 1404, and an end region or nosecone 1408 at a distal end of the catheter body 1404. The nosecone 1408 can be hollow for storing cut tissue that may be later removed and examined and can further include a cutting window 1430 through which a cutting edge 1412 of the cutter 1406 can be exposed. The nosecone 1408 can be attached to the catheter body 1404 through a deflection mechanism, such as a hinge mechanism 1410, to allow the nosecone 1408 to deflect away from the longitudinal axis of the catheter body. In use, this deflection can expose the cutting edge 1412 through the cutting window 1430 and/or radially push the cutter 1406 into a wall of the vessel in which the atherectomy catheter 1400 is inserted. The atherectomy catheter 1400 can further include a stop 1892 (see FIG. 18) to prevent the nosecone from deflecting too far when in the open position.

As shown in FIG. 15B, the atherectomy catheter 1400 can include an imaging element, such as an optical fiber 1514 for OCT, e.g., common path OCT, attached proximal to the cutting edge 1412 of the cutter 1406. The optical fiber 1514 can run through the center of the elongate body, such as through a drive shaft 1516 connected to the cutter 1406, to provide the signal for OCT. The optical fiber 1514 can be attached at the distal end of the catheter, such as in an opening 1518 in the cutter 1406. The optical fiber 1514 can otherwise be free to float within the catheter body 1404. In another embodiment, the optical fiber is attached to a drive shaft within the catheter body. In another embodiment, the optical fiber is off-axis from the drive shaft. A reflective element, such as a mirror 1520, can further be located within the opening 1518 in the cutter 1406 to radially direct light from the optical fiber 1514 into the tissue. The distal end of the optical fiber 1514 can be located less than 3 mm from the cutting edge 1412, such as just adjacent to the cutting edge 1412. By having the imaging element close to the cutting edge, the resulting image closely aligns with the portion of the vessel being cut, providing an advantageous view for the physician during an atherectomy procedure.

The catheter body 1404 of the atherectomy catheter 1400 can include an outer shaft 1522 that can be configured to be turned, such as turned manually or through a driver, such as the magnetic driver described above, to position the distal cutter 1406 and/or the imaging element toward the desired location. A pull shaft 1402 can extend within the outer shaft, and may be concentric with the outer shaft 1522 and inner drive shaft 1516. Using a pull shaft 1402 that is concentric with the shaft system can advantageously circumvent any whip or irregular catheter body rotation that may otherwise be introduced by an off-center component running through the length of the device, i.e. can open and close the nosecone without impacting the directionality of the catheter. A pull-wire can 1524 be attached at one end to the distal end of the pull shaft 1402 and at the other end to a central portion of the nosecone 1408. The pull-wire can run along the outer surface of the catheter. The pull shaft 1402 can be configured to be translated back and forth (proximally and/or distally), such as manually or with a driver, e.g. the magnetic driver above. Such translation of the pull shaft 1402 can pull or push on the pull-wire 1524, thereby causing the nosecone 1408 to deflect away from the central axis in one mode and return to the neutral (undeflected) position in another mode. The nosecone 1408 is thus actuated in and out of the plane of the rest of the catheter to expose or protect the rotating cutter 1406. In one example, this deflection may occur via rotation about the hinge mechanism 1410. For example, the hinge mechanism 1410 can be a pivoting and/or sliding joint that allows deflection of the nosecone 1408 as force is applied by the pull shaft 1402. Deflecting the nosecone 1408 exposes the rotating cutter 1406. This is illustrated in FIG. 14C (showing the catheter in the closed configuration) and FIG. 14D (showing the catheter with the distal tip deflected).

In some variations, the pull shaft can be connected to the nosecone 1408 at a region distal to a joint between the nosecone 1408 and the catheter body 1404, and may act as a hinge (e.g. a living hinge) to pull and bend (or push and extend) the distal tip region.

As noted above, the catheter body 1404 of the atherectomy catheter 1400 can include a drive shaft 1516 extending concentric with the pull shaft 1402, such as extending within the pull shaft 1402. The drive shaft 1516 can be attached to the cutter 1406 (which can be positioned between the catheter body 1404 and the nosecone 1408) and can be configured to rotate the cutter 1406. Rotation of the cutter 1406 can provide cutting due to the rotational motion of the cutting edge 1412 and can provide the rotation necessary to image the inner diameter wall components of a vessel with the imaging element. The drive shaft 1516 can be rotated at up to 2,000 rpm, such as approximately 1,000 rpm in a single direction, though rotation in both directions and at different speeds is possible.

Having a separate outer shaft, pull shaft, and drive shaft can advantageously separate the rotational motion of the cutting element from the translational motion required to activate/deactivate the deflection mechanism. This separation can avoid placing tension or compression on the drive shaft during the axial translation that is used to deflect/undeflect the nosecone, which can cause distortion in the resulting image. This separation can further simplify the distal mechanism design relative to having all elements (pull and drive) combined in one drive system, enabling the device to be scaled down to reduced sizes for small vessels, such as coronary arteries.

In some embodiments, a monorail guidewire lumen 1844 is located on the distal portion and/or nosecone 1408 of the device. Positioning the guidewire in a monorail lumen 1844 provides more room in the catheter body 1404 for the optical fiber and pull shaft elements. Further, positioning the guidewire lumen 1844 opposite the cutting window 1430 provides an additional element that is visible via OCT for directing the cutter toward a lesion of interest, as discussed further below. When the monorail guidewire lumen is used, the guidewire can extend along the outside of the catheter body, such as be free floating until it reaches the guidewire lumen (as shown and discussed with respect to FIGS. 20H-K below).

Figure 16A:
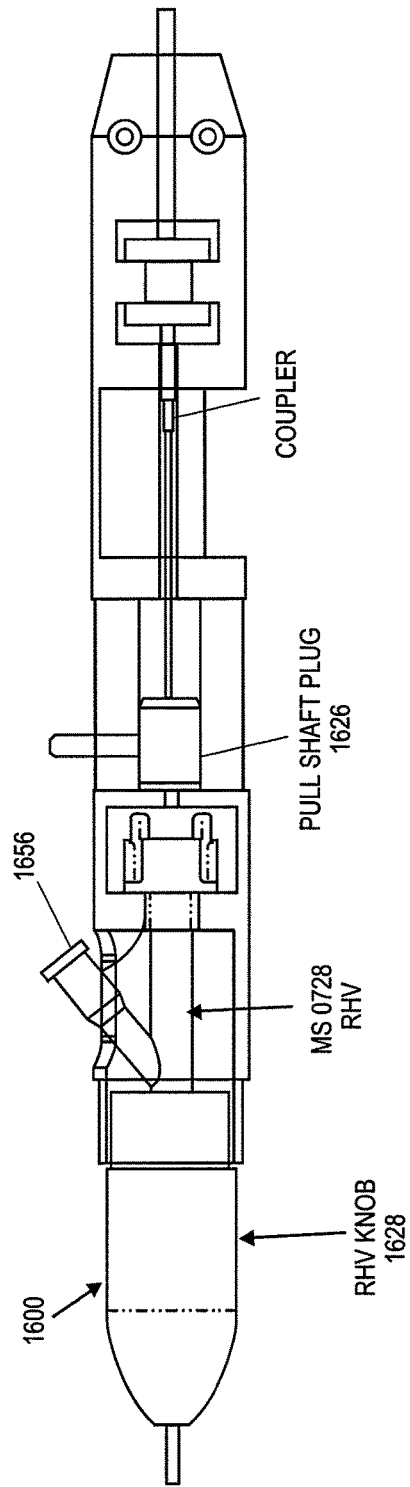
FIG. 16A shows a handle used to control the pull shaft of the catheter of FIGS. 14A-15B.
Figure 16B:
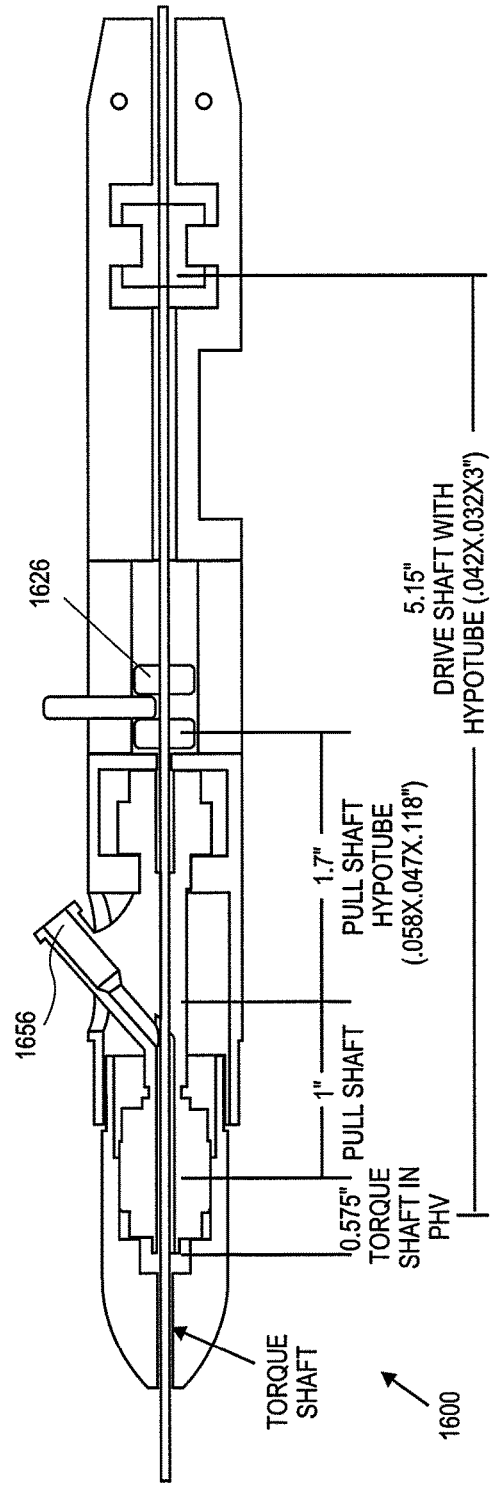
FIG. 16B is a cross section of the handle shown in FIG. 16A.

Referring to FIGS. 16A and 16B, a handle 1600 can be used to control the activation of the pull shaft. The pull shaft can be attached to the pull shaft "plug" 1626 in the handle 1600. An extension from this plug 1626 can be accessed by the user and translated proximally/distally along the length of the handle either manually or through a driver, such as the magnetic driver described above. This proximal and distal movement of the pull shaft can result in the nosecone deflecting/undeflecting. The translation plug 1626 in the handle 1626 can be separate from a mechanism that moves the cutting/imaging element to move the cutter to pack tissue into the nosecone. Thus, the pull shaft plug 1626 enables manipulation of the nosecone deflection angle independently from the drive system that controls cutting and imaging. A rotation mechanism, such as a knob 1628 can be used to rotate the outer shaft (again either manually or with a driver such as the magnetic driver described above) to direct the cutter to the proper location.

Figure 17B:
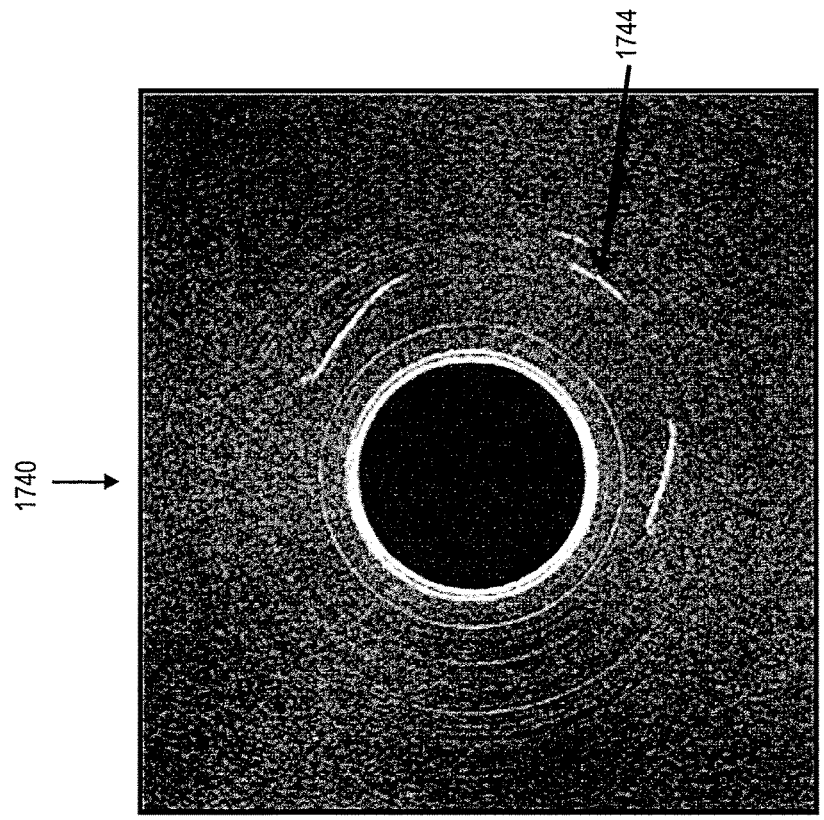
FIG. 17B shows an OCT image produced from the atherectomy catheter of FIGS. 14A-15B with the nosecone opened (cutter activated) as indicated by the bright reflection from the off-centered housing.
Figure 17A:
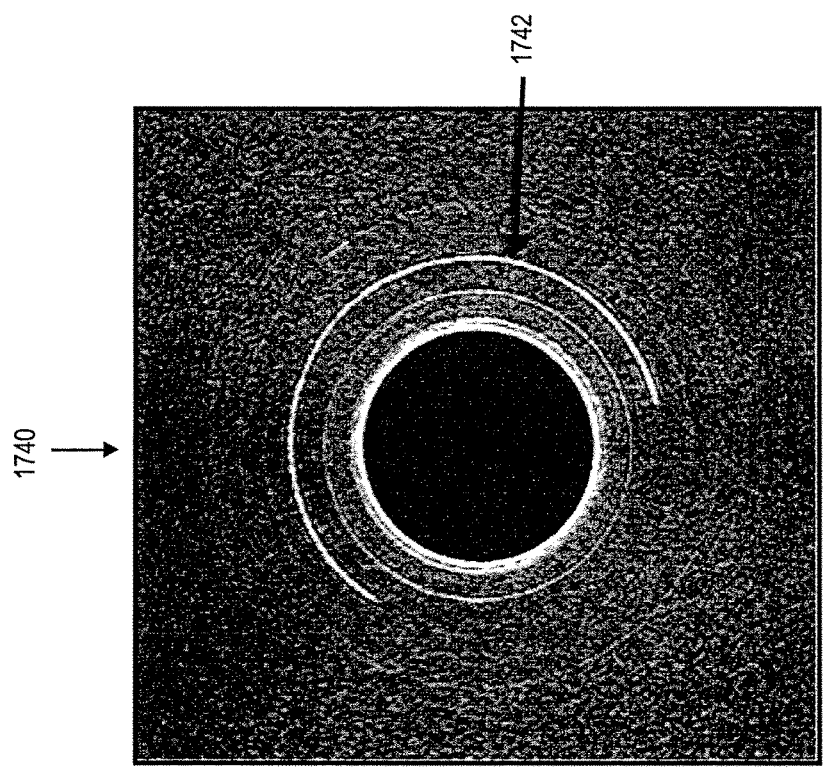
FIG. 17A shows an OCT image produced from the atherectomy catheter of FIGS. 14A-15B with the nosecone closed (cutter packed) as indicated by the bright reflection from the housing.

In this example, the imaging sensor of the OCT imaging sub-system is coupled just proximal to the rotating cutter. Thus, the catheter may image with the distal tip either in-line with the rest of the catheter or deflected (exposing the cutter), or in some variations, the imaging system may provide a somewhat restricted view when the distal tip is deflected and cutting is engaged. This may occur when the distal tip and/or pull shaft may occlude part of the OCT imaging sensor as it rotates around the distal tip, and may be beneficial as providing direct feedback to the operator that the cutter is engaged. For example, referring to FIGS. 17A and 17B, rotation of the imaging element on of the atherectomy catheter 1400 can result in an image of the interior of the vessel in which the atherectomy catheter is inserted. Referring to FIG. 17A, when the nosecone is closed, a mark 1742 may display on the OCT image 1740. The mark 1742 will correspond to the portion of the housing that extends around the nosecone, i.e. to the portion that is not occupied by the cutting window. Because this mark 1742 will always be opposite to the location of the cutter, the mark 1742 can be used to steer the atherectomy cutter to the desired location via rotation of the outer shaft toward the desired location. Referring to FIG. 3B, when the nosecone is open, the OCT image 1750 a similar but shorter mark 1744 may display that corresponds to the housing. This mark 1744 can again be used to steer the atherectomy cutter to the desired location. Further, the length of this mark 1744 may be used to indicate how far the nosecone is deflected away from the main catheter axis, providing a real-time tool to gauge cut depth.

Figure 18:
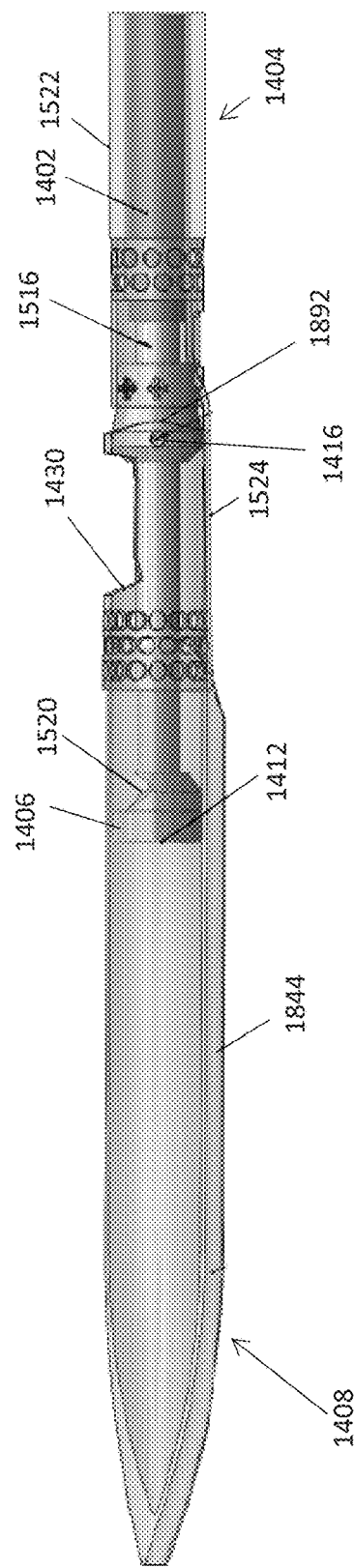
FIG. 18 shows an atherectomy catheter having a pull-wire activation mechanism and a driveshaft and cutter extendable into the nosecone.

In some embodiments, referring to FIG. 18, one or more of the shafts of the atherectomy catheter 1400 can be translated axially to pack dissected tissue into the nosecone 1408. Thus, as shown in FIG. 18, the drive shaft 1516 can be configured to be translated axially (manually or through a driver such as the magnetic driver described above), thereby translating the cutter 1406 axially, such that the distal surface of the cutter can be used to advance and pack the cut tissue into the nosecone 1408. If the drive shaft 1516, and thus the cutter 1406 and imaging element, has been pushed into the nosecone 1408, then the monorail guidewire lumen 1844 can be used as a marker to assess the location of the cutter.

Figure 19:
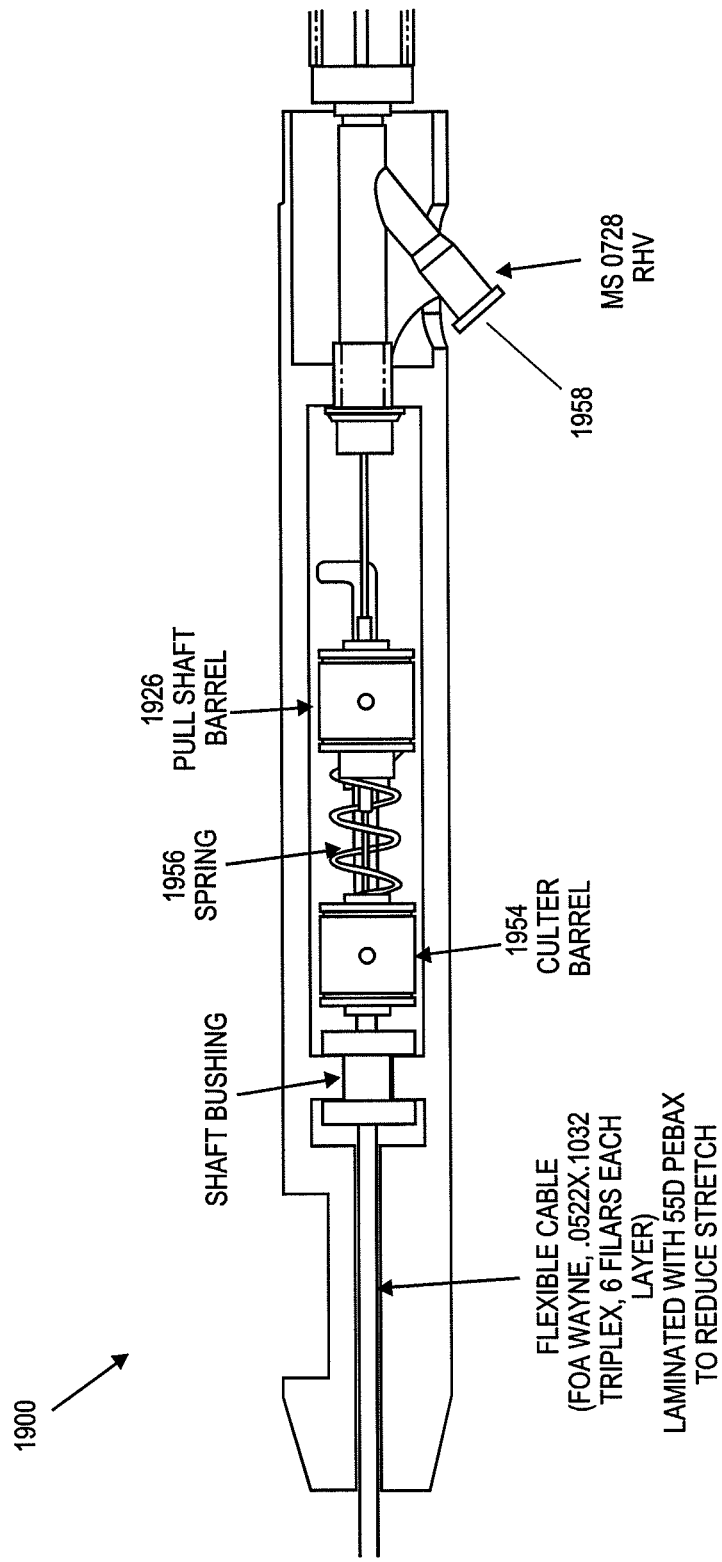
FIG. 19 shows a handle used to control the pull shaft of the catheter of FIG. 18 to open and close the nosecone as well as a slider to move the driveshaft forward to pack tissue into the nosecone.
Figure 20A:
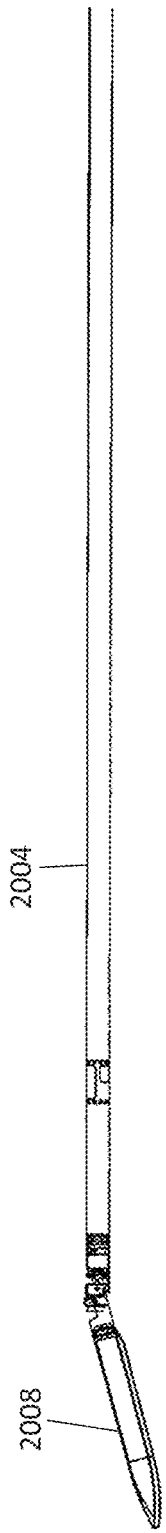
Figure 20B:
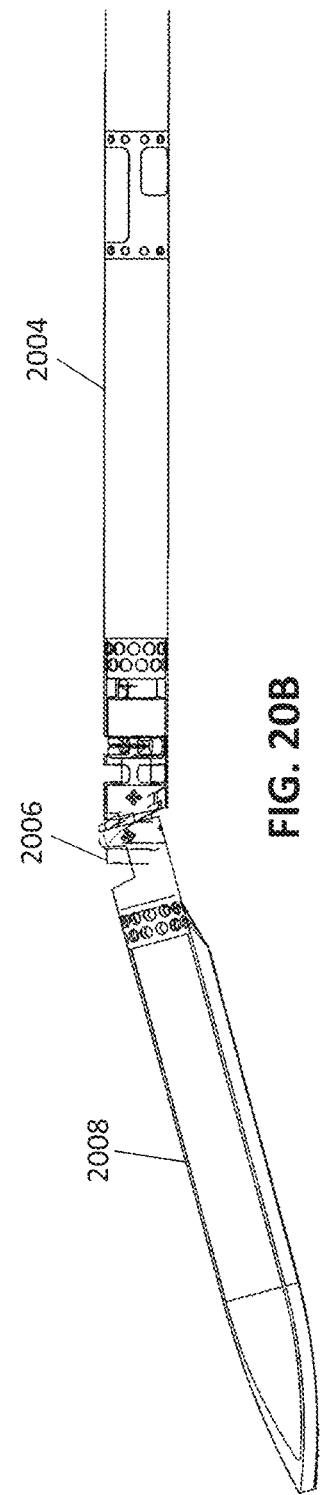
Figure 20C:
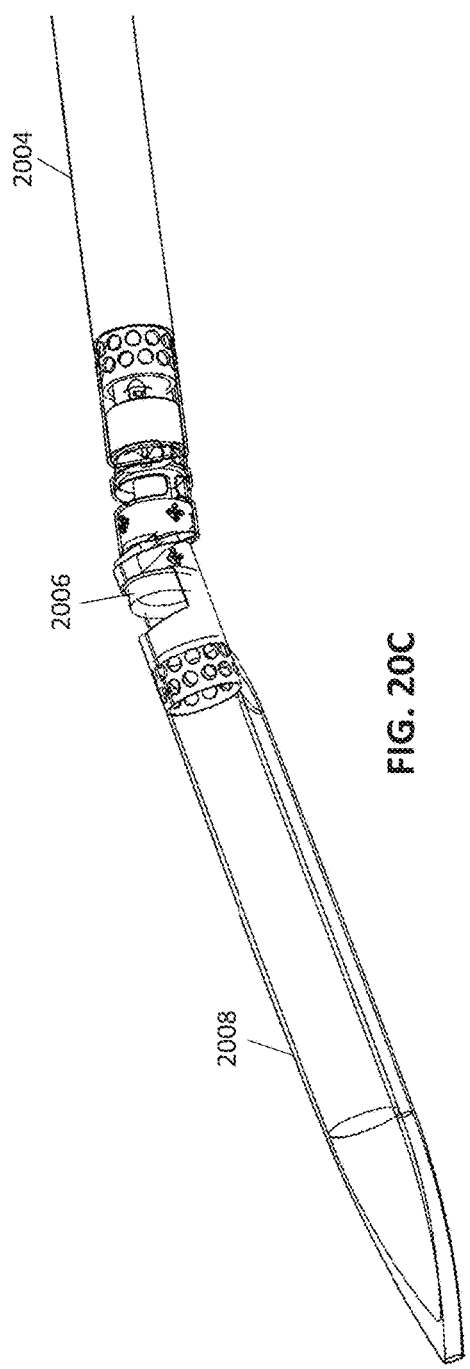
Figure 20D:
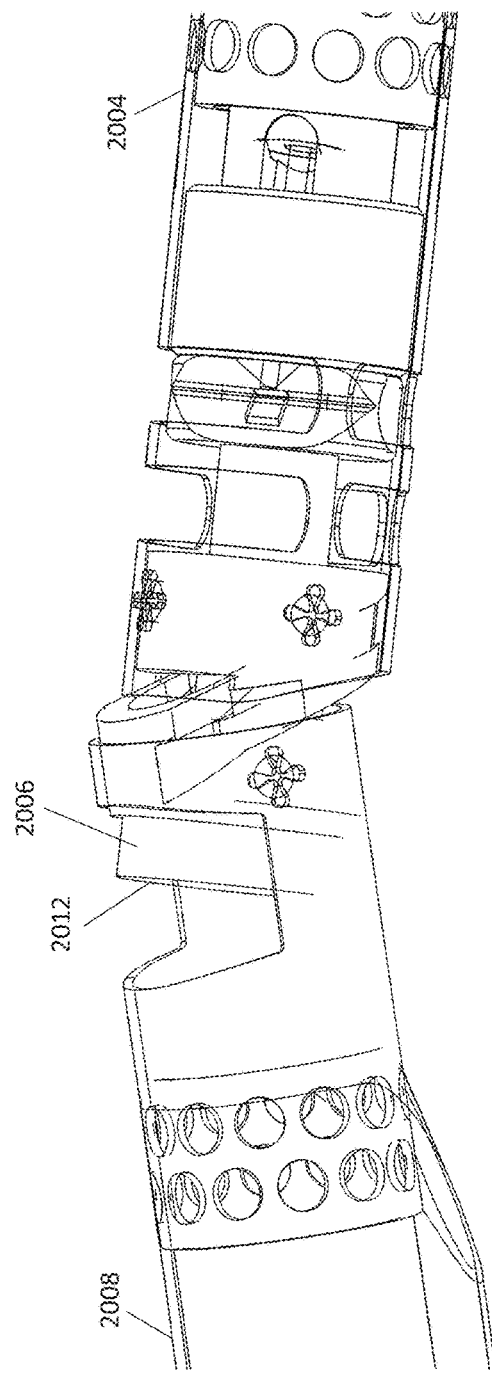

Referring to FIG. 19, a handle 1900 can be configured to enable independent control of the drive shaft and pull shaft translation. This handle 1900 is comparable to that shown in handle 1600 with the addition of a "cutter barrel" 1954 that enables user interaction with the drive shaft that controls the cutter/imaging element location. This cutter barrel 1954 may be translated proximally/distally to open/pack the cutter and imaging element. That is, in use, the cutter barrel 1954 can be pulled proximally to pull the cutter back, and then the pull shaft barrel 1926 can be pulled proximally to drop the nosecone and expose the cutter (pulling the cutter barrel proximally before pulling the pull shaft barrel 1926 proximally ensures proper positioning of the cutter when the nosecone is dropped down). To close the nosecone, the opposite can be done—push the pull shaft barrel 1926 distally to close the nosecone and the push the cutter barrel 1954 forward to pack tissue. A spring 1956 between the pull shaft barrel 1926 and the cutter barrel 1954 can ensure that the cutter is pulled all the way back when the nosecone is opened and keep the cutter pulled back.

The catheter 1400 can further include a flush port close to the cutter. The handle 1600 or the handle 1900 may contain a flush entry port 1658, 1958 that enables the delivery of saline and/or contrast to the distal imaging element location. Flushing at the distal location may be utilized to displace blood to provide a clear OCT image.

Catheters for Use with Non-Contact Drive System and/or Pull-Wire Activation

Other catheter embodiments can be used with either the non-contact drive systems described herein with respect to FIGS. 1-13 and/or the pull-wire activation mechanism described with respect to FIGS. 14A-19.

For Example, FIGS. 20A-20K illustrate an atherectomy catheter 2000. The nosecone 2008 is deflectable from the catheter body 2004 to expose a rotating cutting edge 2012 of a cutter 2012. The cutter 2006 and imaging chassis, to which the end of the optical fiber forming the OCT imaging sensor are coupled, together to rotate. A drive shaft 2016 rotates both the sensor and cutter. In FIGS. 9-20 the system is configured so that lateral (proximal-to-distal) movement of the drive shaft 2016 causes displacement of the nosecone 2008, exposing or protecting the rotating ring cutter 2006.

The optical fiber of the atherectomy catheter 2000 may be held within the central lumen region of the drive shaft 2016 (which is itself within the center of the catheter). In these variations, the optical fiber may be allowed to twist upon itself as the distal tip rotates. The distal end of the optical fiber may be fixedly mounted to the rotating cutter 2006. The end of the fiber may therefore be extended up through the optical fiber chassis or housing to a region near the perimeter of the chassis where it can be directed to a mirror element 2020 to direct the beam out of the catheter and into the surrounding tissue (e.g. vessel). An appropriate epoxy or resin may be used to hold the end of the fiber in place.

For example, when rotating the drive shaft to rotate the cutter 2006 and/or OCT imaging sensor, the drive shaft 2016 may be driven only in one direction. In other embodiments, the shaft 2006 can be rotated approximately 300-500 times clockwise, then the direction of rotation may be reversed, and the cycle (clockwise, counterclockwise) repeated. Thus, an optical fiber within the lumen of the drive shaft may twist 300-500 times then reverse. The fiber may twist in the hollow shaft, which may allow more turns than variations in which wrapping around the drive shaft is used (as illustrated and discussed above). Surprisingly this twisting and untwisting within the lumen may be performed repeatedly without substantially adversely affecting performance of the OCT system and fiber optic. Although the optical fiber is in the center of the catheter (e.g., the center of the drive shaft), it is still off-axis at the distal end of the catheter, where the imaging element is displaced a bit from the edge of the device, as illustrated.

The catheter 2000 can be configured such that movement of the driveshaft 2016 (rotation or lateral movement) and/or movement of the outer shaft (rotation or lateral movement) can be conducted using the magnetic drive system described above.

Figure 14A:
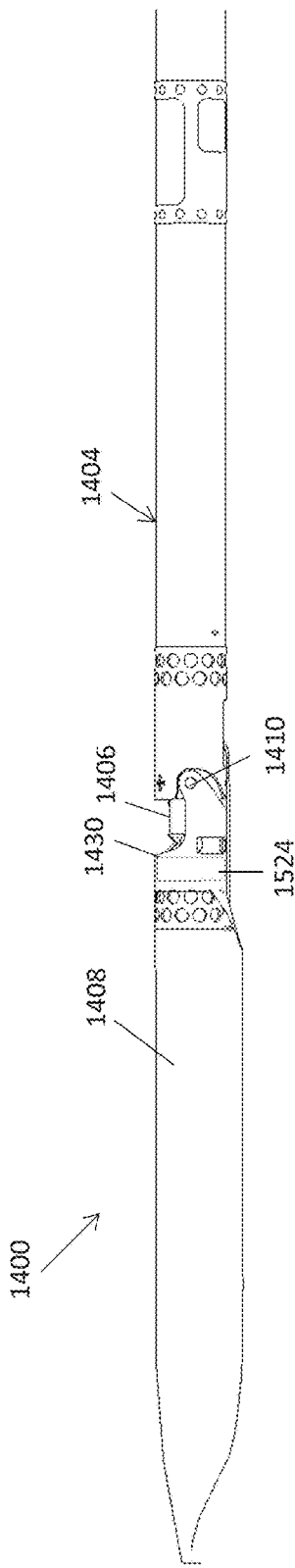
Figure 14B:
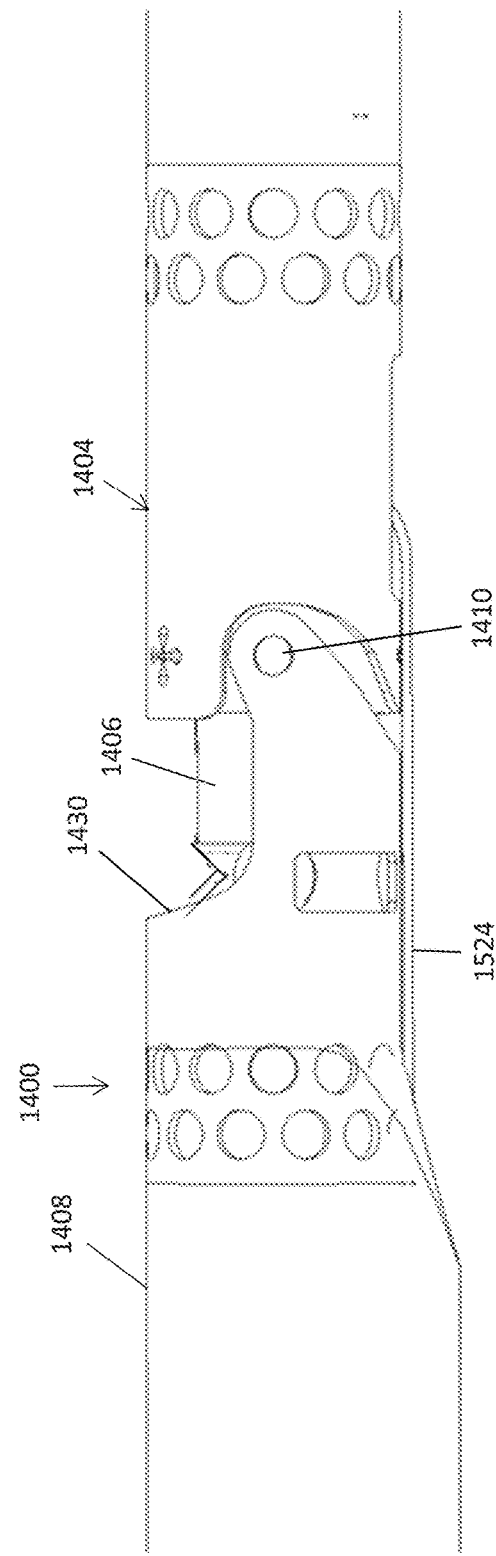
Figure 14E:
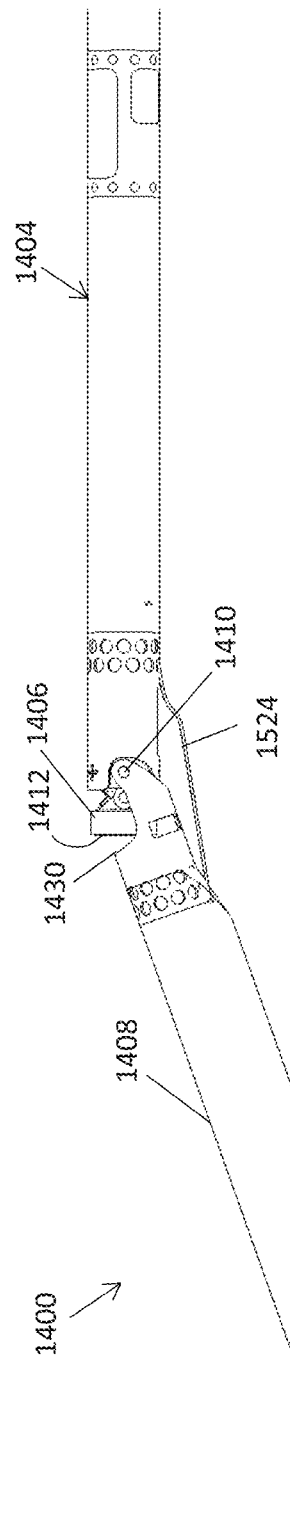

As described above with respect to the atherectomy device 1400 of FIG. 14, the atherectomy device 2000 can include a monorail guidewire channel in the nosecone. An exemplary guidewire 2086 is shown in FIGS. 20G-K extending alongside the catheter.

Further, in some embodiments, the catheter 2000 can be fitted with a pull shaft and/or pull-wire to deflect the nosecone 2008.

A similar atherectomy device is described in co-pending U.S. application Ser. No. 13/175,232, filed Jul. 1, 2011, and titled "ATHERECTOMY CATHETERS WITH LONGITUDINALLY DISPLACEABLE SHAFTS," which is incorporated by reference herein.

Figure 21C:
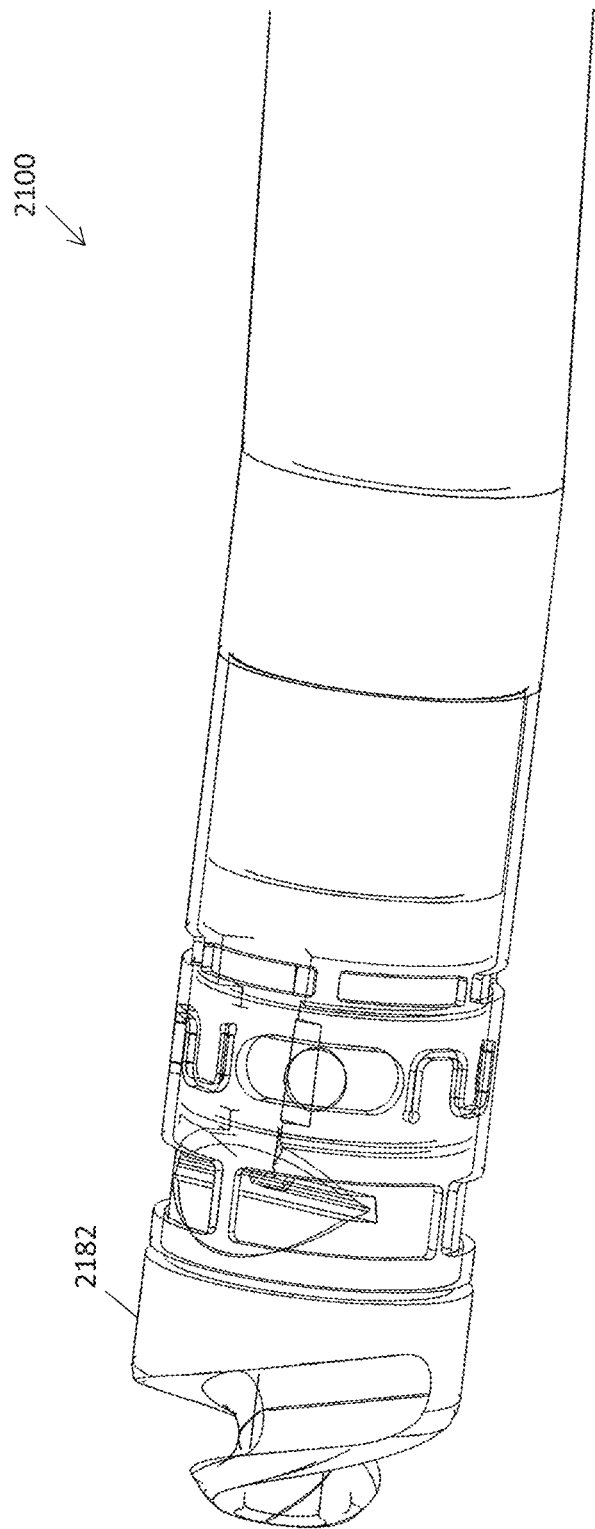
Figure 21D:
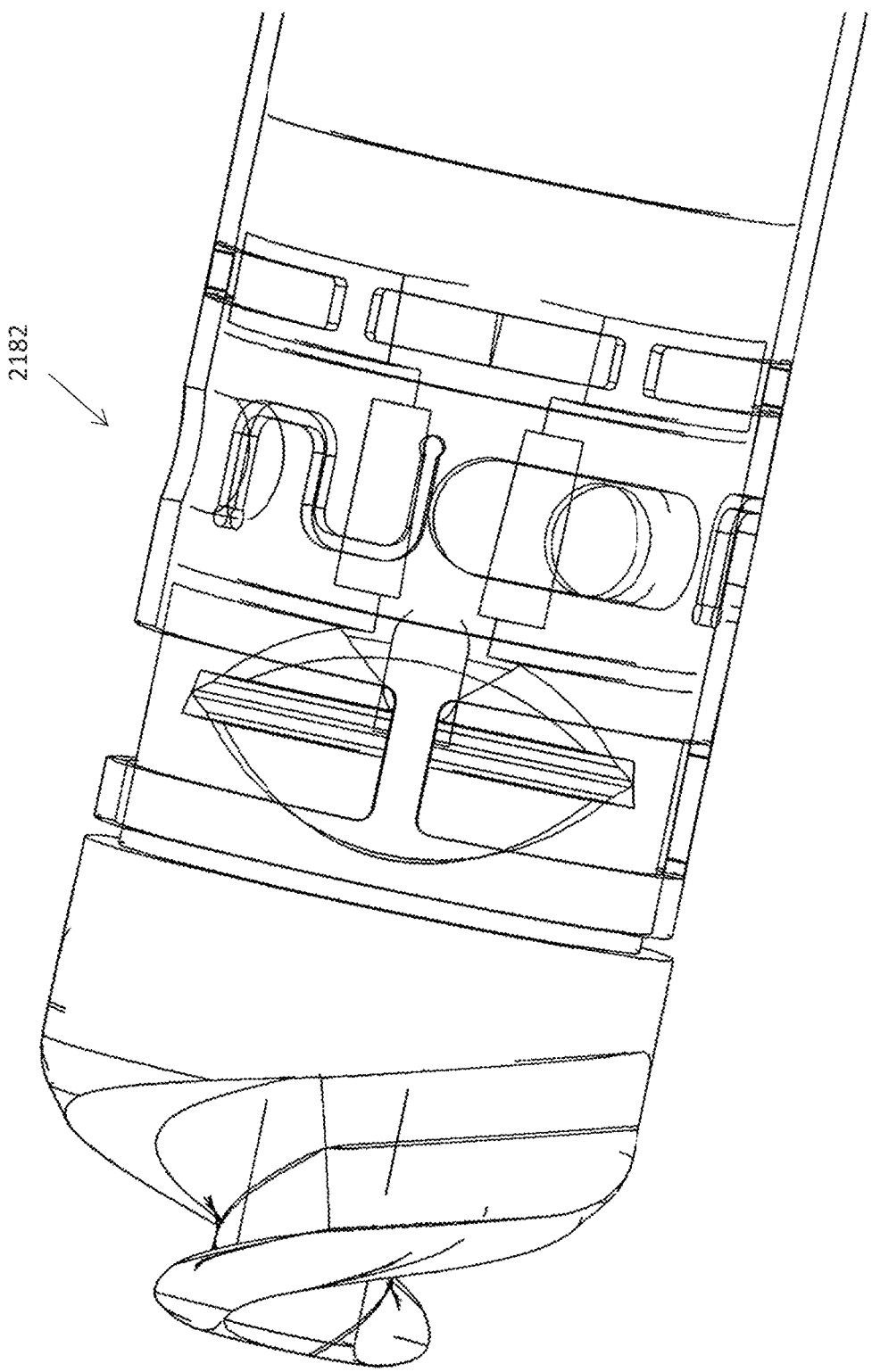
Figure 21E:
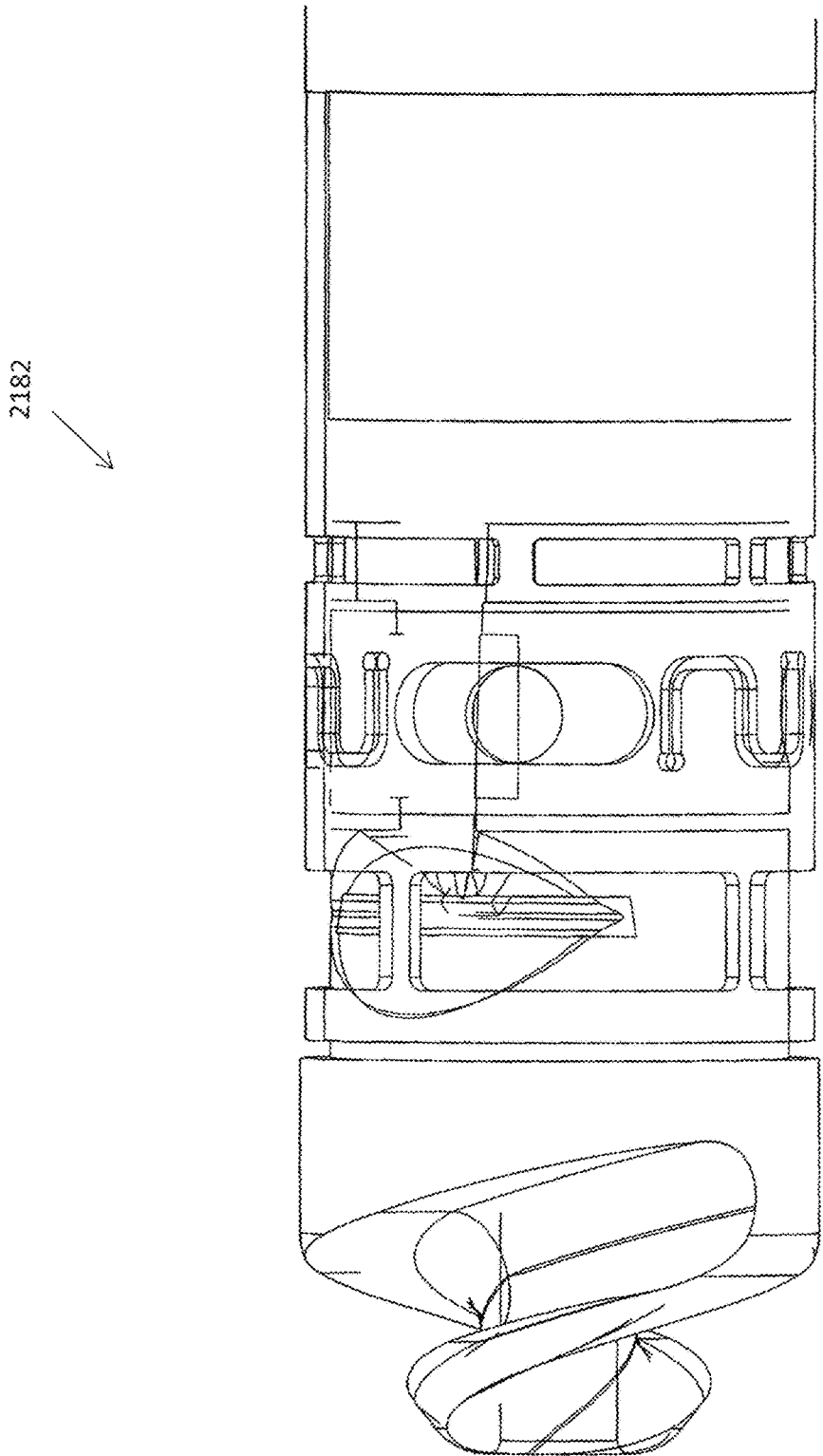
Figure 21F:
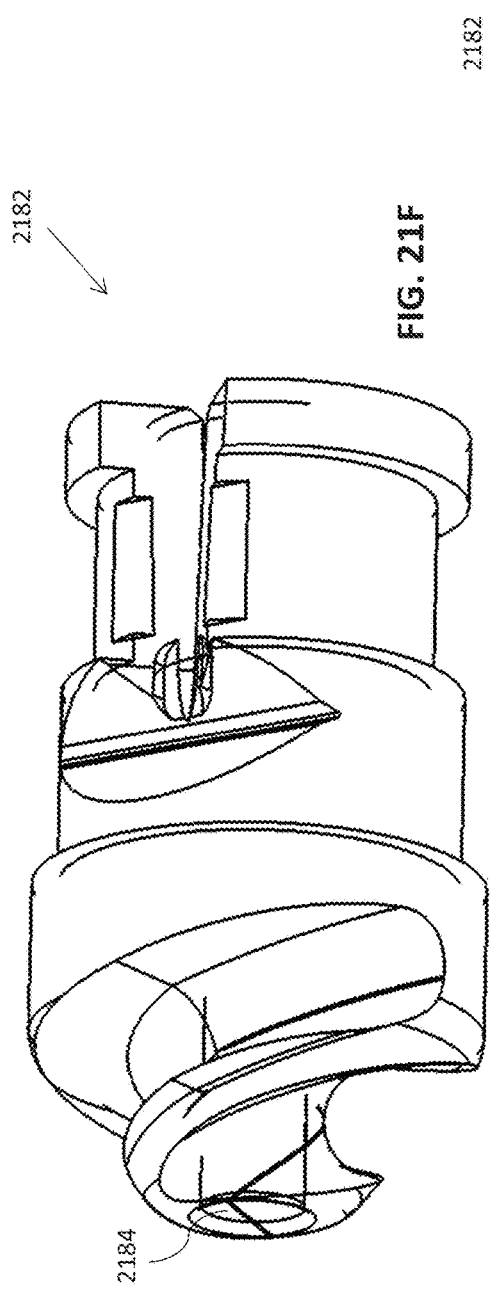
Figure 21G:
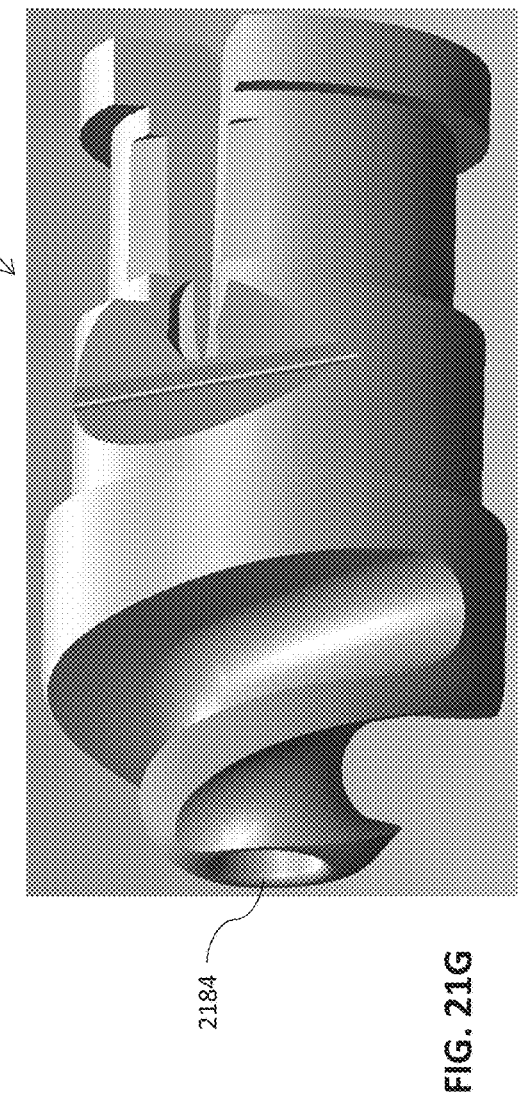

For example, FIGS. 21A-I illustrate another variation of a catheter 2100 that could be used with the magnetic drive system and/or pull-wire mechanism described above. The catheter 2100 is configured as a guidewire placement catheter that includes a rotatable distal tip 2182 and a central lumen 2184 through which a guidewire may be passed, as well as a rotating OCT imaging sensor which includes a fiber optic cable. Devices such as this may be used to cross and position a guidewire through a chronic total occlusion (CTO) without damaging the blood vessel, as would otherwise occur if the guidewire were forced through a CTO. Such devices may be referred to as "CTO crossing devices having imaging" or "CTO imaging and crossing devices." FIG. 21A shows a side view of one variation of a CTO imaging and crossing device for placing a guidewire across a CTO. In this example, the proximal end includes a handle 2186 or controller (shown here as a housing that includes sensor and gearing elements to control operation of the device). FIG. 21B shows an enlarged view of the distal end of the device of FIG. 21A, as do FIGS. 21C-21E. In these figures, the rotatable distal tip 2182 includes a helical cut-out region for engaging (and passing through) CTO material. FIGS. 21F and 21G show just the tip region (rotatable distal tip) of this device. The outer edges of the tip are smooth and curved, to prevent damage to vessel walls. In this example, the tip also includes a mount for the OCT imaging optical fiber, which may form the OCT imaging sensor. Thus, the distal end of the OCT imaging optical fiber may be fixed (e.g., glued, epoxied, etc.) to the rotatable distal tip.

Figure 21I:
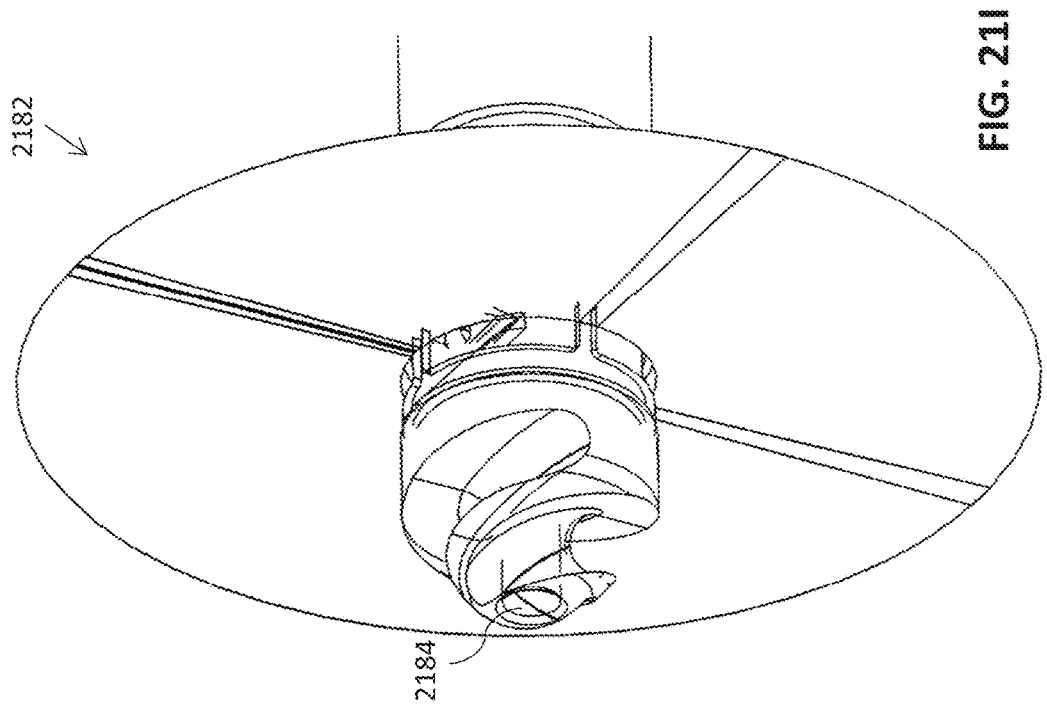
Figure 21H:
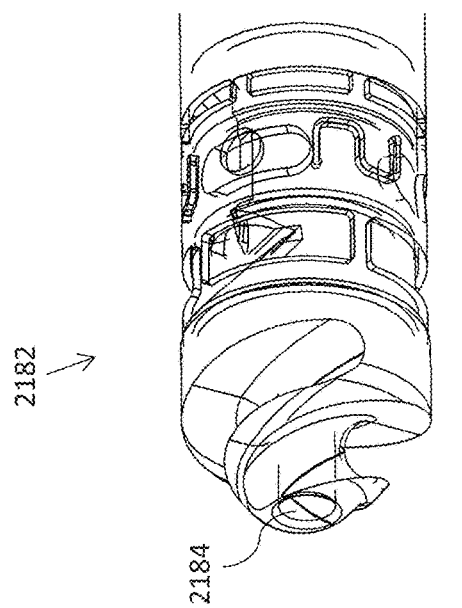

FIG. 21H shows an enlarged view of the distal end of the tip. FIG. 21I shows the same view as FIG. 21H, only with a circular disk indicating the area to be imaged by the rotating OCT sensor (fiber end) as the tip is rotated. Thus, this system may provide a 360° view of the region around the distal tip (e.g., the walls of the vessel, including into the vessel wall). The OCT image may penetrate some depth into the vessel, and therefore allow resolution of different structures at and within the vessel wall. In this example, the viewing field is interrupted by three regions that are blocked from imaging; these regions are arranged to allow fiducial markings around the perimeter; the entire catheter tip region may be rotated to change the position of these occluded regions.

Activation of the distal tip 2182 can be controlled by a driver, such as the magnetic driver described above. Further, the catheter 2100 could be fitted with a pull-wire mechanism similar to that described above, for example if there were a housing on the distal end of the catheter to protect the rotating distal tip when not in use.

A similar occlusion-crossing device is described in co-pending U.S. application Ser. No. 13/433,049, filed Mar. 28, 2012, and titled "OCCLUSION-CROSSING DEVICES, IMAGING, AND ATHERECTOMY DEVICES", now Publication No. US-2012-0253186-A1 which is incorporated by reference herein.

It is to be understood that other catheter designs for use with the magnetic drive system and/or pull-wire deflection mechanism are possible.

CONCLUSION

Described herein are devices, including at least some specific exemplary devices, in which dimensions are provided. It is to be understood that these dimensions may be varied while staying within the scope of the invention as generally described. Thus, these figures may not be shown to scale. Unless otherwise indicated, these dimensions are intended as merely illustrative, and not limiting.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. An atherectomy catheter comprising:
   an elongate catheter shaft;
   a deflectable distal tip coupled to the elongate shaft at a hinge;
   a rotatable cutter proximal to the distal tip;
   a cutter drive shaft configured to rotate the rotatable cutter wherein the drive shaft is hollow, and wherein an optical fiber for optical coherence tomography imaging extends within the drive shaft;

a pull shaft positioned radially inwards of the elongate catheter shaft and concentric with the drive shaft; and a pull-wire eccentric with the drive shaft and having a proximal end and a distal end, the distal end coupled to the distal tip at a location distal to the hinge and the proximal end coupled to a distal end of the pull shaft at a location proximal of the hinge such that the pull-wire axially spans the hinge, wherein the pull shaft is configured to proximally pull the pull-wire to deflect the distal tip at the hinge, thereby exposing the rotatable cutter.

2. The atherectomy catheter of claim 1, wherein the optical fiber is coupled to the rotatable cutter but is otherwise free to float within the drive shaft.

3. The atherectomy catheter of claim 1, wherein the optical fiber extends along a proximal to distal length of the catheter off-axis from the drive shaft.

4. The atherectomy catheter of claim 1, wherein the pull shaft and pull-wire are movable with respect to the drive shaft.

5. The atherectomy catheter of claim 1, wherein the pull shaft deflects the distal tip without rotating the catheter.

6. An atherectomy catheter comprising:
a catheter body;
a deflectable distal tip, wherein the deflectable distal tip is hinged to a distal region of the catheter body at a pivot point;
a rotatable cutter proximal to the deflectable distal tip, the rotatable cutter having a distal cutting edge;
a pull-wire mounted to the deflectable distal tip and extending proximally lateral to the cutter and pivot point, wherein the pull-wire is pulled proximally to deflect the deflectable distal tip at the pivot point and thereby move the distal cutting edge from a protected configuration to an exposed configuration;
a pull shaft extending within and along the length of the catheter body, wherein the pull shaft pulls the pull-wire proximally to deflect the distal tip; and
an optical fiber for optical coherence tomography imaging attached to the cutter proximal to the distal cutting edge.

7. The atherectomy catheter of claim 6, wherein the optical fiber is attached to the rotatable cutter but is otherwise free to float within the catheter body.

8. The atherectomy catheter of claim 6, wherein the pull-wire and pull shaft are movable with respect to the outer shaft of the catheter body.

9. The atherectomy catheter of claim 8, wherein the pull shaft is concentric with the outer shaft.

10. The atherectomy catheter of claim 6, further comprising a drive shaft configured to rotate the rotatable cutter.

11. The atherectomy catheter of claim 10, wherein the drive shaft is hollow, and wherein the optical fiber extends within the drive shaft.

12. The atherectomy catheter of claim 6, wherein the pull-wire deflects the distal tip without rotating the catheter.

13. The atherectomy catheter of claim 6, wherein deflection of the distal tip exposes the distal cutting edge.

14. An atherectomy catheter comprising:
an elongate catheter shaft;
a deflectable distal tip coupled to the elongate shaft at a hinge;
a rotatable cutter proximal to the distal tip;
a cutter drive shaft configured to rotate the rotatable cutter;
a pull shaft positioned radially inwards of the elongate catheter shaft and concentric with the drive shaft; and
a pull-wire eccentric with the drive shaft and having a proximal end and a distal end, the distal end coupled to the distal tip at a location distal to the hinge and the proximal end coupled to a distal end of the pull shaft at a location proximal of the hinge such that the pull-wire axially spans the hinge, wherein the pull shaft is configured to proximally pull the pull-wire to deflect the distal tip at the hinge, thereby exposing the rotatable cutter;
wherein the pull shaft and pull wire are movable with respect to the drive shaft; and
wherein the pull shaft extends along an entire length of the elongate catheter shaft.

* * * * *